(12) United States Patent
Zock et al.

(10) Patent No.: US 7,085,765 B2
(45) Date of Patent: Aug. 1, 2006

(54) METHODS TO INCREASE THE CAPACITY OF HIGH CONTENT CELL-BASED SCREENING ASSAYS

(75) Inventors: Joseph Zock, Mars, PA (US); Megan Weiss, Pittsburgh, PA (US)

(73) Assignee: Cellomics, Inc., Pittsburgh, PA (US)

( * ) Notice: Subject to any disclaimer, the term of this patent is extended or adjusted under 35 U.S.C. 154(b) by 448 days.

(21) Appl. No.: 10/096,378

(22) Filed: Mar. 12, 2002

(65) Prior Publication Data

US 2002/0177174 A1   Nov. 28, 2002

Related U.S. Application Data

(60) Provisional application No. 60/274,969, filed on Mar. 12, 2001.

(51) Int. Cl.
*G01N 33/44* (2006.01)
*C12Q 1/00* (2006.01)

(52) U.S. Cl. .............................. 707/19; 435/4
(58) Field of Classification Search ................... 702/19
See application file for complete search history.

(56) References Cited

U.S. PATENT DOCUMENTS

| 5,491,084 A | 2/1996 | Chalfie et al. |
| 5,989,835 A | 11/1999 | Dunlay et al. |
| 6,103,479 A | 8/2000 | Taylor et al. |
| 6,210,910 B1 | 4/2001 | Walt et al. |
| 6,416,959 B1 * | 7/2002 | Giuliano et al. ............ 435/7.2 |

FOREIGN PATENT DOCUMENTS

| WO | WO 98/38490 | 9/1998 |
| WO | WO 00/03246 | 1/2000 |

OTHER PUBLICATIONS

Kapur et al. Streamlining the Drug Discovery Process by Integrating Miniaturization, High Throughput Screenin, High Content Screening, and Automation on the CellChip System. Biomedial Microdevices. 1999. vol. 2, No. 2, pp. 99-109.*
Barak et al. (1997), *J. Biol. Chem.* 272:27497-27500.
Barber et al. (1996), *Neuroscience Letters* 207:17-20.
Bright et al. (1996), *Cytometry* 24:226-233.
Cubitt et al. (1995), *Trends in Biochemical Science* 20:448-455.
Daaka et al. (1998), *J. Biol. Chem.* 273:685-688.
Farkas et al. (1993) *Ann. Rev. Physiol.* 55:785.
Giuliano and Taylor (1995), *Curr. Op. Cell Biol.* 7:4-12.
Giuliano et al. (1990) *Optical Microscopy for Biology.* pp. 543-557.
Giuliano et al. (1995) *Ann. Rev. Biophys. Biomol. Struct.* 24:405-434.
Giuliano, et al., (1997) *J. Biomol. Screening,* 2(4):249-259.
Hahn et al (1992) *Nature* 359:736-738.
McNeil (1989) *Methods in Cell Biology*, 29:153-173.
Taylor, et al., (1992), American Scientist, 80: 322-335.
Taylor, et al., (1996), Intl. Soc. For Optical Engineering, 2678: 15-27.
Waggoner et al. (1996) *Hum. Pathol.* 27:494-502.
Wiemer et al. (1997) *J. Cell Biol.* 136:71-80.

* cited by examiner

Primary Examiner—Ardin H. Marschel
Assistant Examiner—Anna Skibinsky
(74) Attorney, Agent, or Firm—McDonnell Boehnen Hulbert & Berghoff LLP

(57) ABSTRACT

The present invention involves the pooling of multiple high content cell-based screening assays, and carrying out a primary screen in a one or more channels of a fluorescence detection device, which drastically increases the number of simultaneous high content cell-based screening events that can be carried out. Subsequent deconvolution of primary screen "hits" (ie: those wells or locations on an array of locations in which the one or more test compounds caused a change in the fluorescence signal(s) from the fluorescent reporter molecules in the cells) enables much more rapid generation of high content cell screening data than was previously possible, and at significantly reduced costs.

22 Claims, 6 Drawing Sheets

Figure 1
Multiple Plate, 4 Fluorescent Reporter Molecules (F1-F4), 1 Reporter Set (R1)
a) Primary Screen
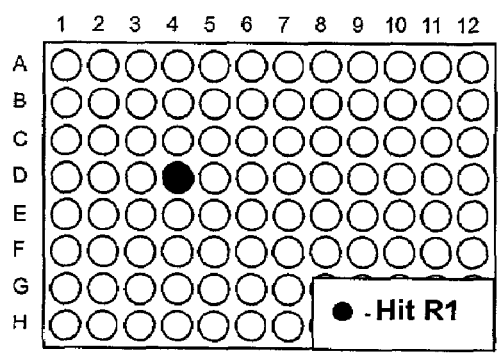
Plate 1
F1-F4, R1
b) Deconvolve
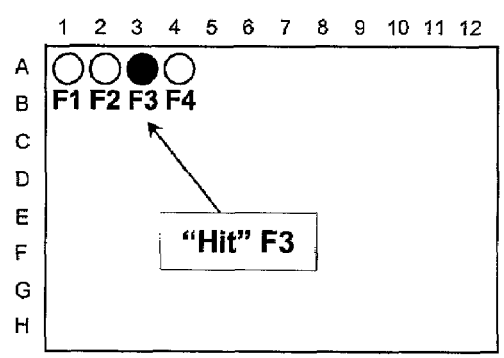
Plate 2

Figure 2
Multiple Plate, 4 Fluorescent Reporter Molecules (F1-F4),
2 Reporter Sets (R1,R2)
a) Primary Screen
b) Deconvolve
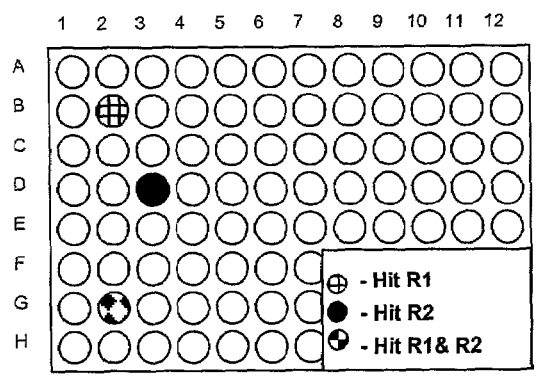
Plate 1
F1/F2,R1;F3/F4,R2
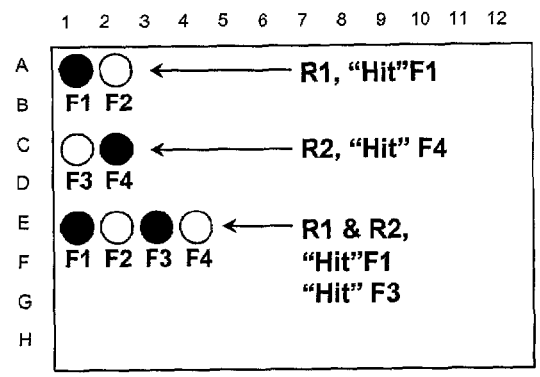
Plate 2

Single Plate, 3 Fluorescent Reporter Molecules (F1-F3),
1 Reporter Set (R1)

a) Primary Screen b) Deconvolve

Plate 1
F1-F3,R1

Plate 1, 2nd Pass
F1,F4
F2,F5

Figure 4

Traditional Method

4 screens, each with 1 Fluorescent Reporter Molecule
(10 plate compound library)

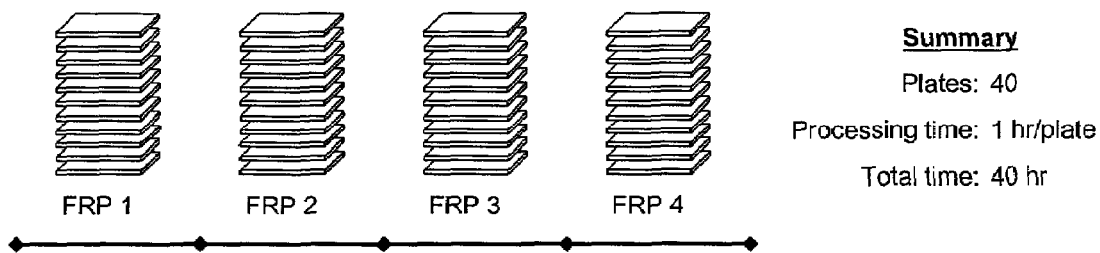

Summary

Plates: 40

Processing time: 1 hr/plate

Total time: 40 hr

Methods of the Present Invention

1 primary screen with 4 Fluorescent Reporter Molecule (10 plate compound library)

Summary

Plates: 12

Processing time: 1 hr/plate

Total time: 12 hr

Timesavings

| | |
|---|---|
| Traditional Method | 40 hrs |
| Methods of the Present Invention | 12 hrs |
| Difference | 28 hrs ← 70% decrease |

METHODS TO INCREASE THE CAPACITY OF HIGH CONTENT CELL-BASED SCREENING ASSAYS

CROSS REFERENCE

This application claims priority to U.S. Provisional Patent Application 60/274,969 filed Mar. 12, 2001.

FIELD OF THE INVENTION

The present invention related to the fields of drug discovery, cell biology, and molecular biology.

BACKGROUND OF THE INVENTION

Drug discovery is a long, multiple step process involving identification of specific disease targets, development of an assay based on a specific target, validation of the assay, optimization and automation of the assay to produce a screen, high throughput screening of compound libraries using the assay to identify "hits", hit validation, and hit compound optimization. The output of this process is a lead compound that goes into pre-clinical studies and, if validated, eventually into clinical trials. In this process, the screening phase is distinct from the assay development phases, and involves testing compound efficacy in living biological systems.

Historically, drug discovery is a slow and costly process, spanning numerous years and consuming hundreds of millions of dollars per drug created. Developments in the areas of genomics, proteomics, and high throughput screening have resulted in increased capacity and efficiency in the areas of target identification, structure-function predictions, and volume of compounds screened. Significant advances in automated DNA sequencing, PCR application, positional cloning, hybridization arrays, and bioinformatics have greatly increased the number of genes (and gene fragments) encoding potential drug screening targets. However, the basic scheme for drug screening remains the same.

The next level of biological complexity is the cell, and sophisticated automated methods for cell-based screening based on imaging of fluorescent reporter molecules in cells have recently been developed. (See, for example, U.S. Pat. Nos. 5,989,835 and 6,103,479, as well as published PCT application Nos. WO 98/38490, WO 00/03246, WO 00/17643, WO 00/26408, WO 00/50872, WO/00/70342, WO 00/17624, and WO/00/60356.) The process of implementing such cell-based assays is also referred to as high content screening ("HCS"), and addresses a need for more detailed information about the temporal-spatial dynamics of cell constituents and processes, and how they are affected by potential drug candidates.

HCS automates the extraction of multicolor luminescence information derived from specific luminescence-based reagents incorporated into cells (Giuliano and Taylor (1995), *Curr. Op. Cell Biol.* 7:4; Giuliano et al. (1995) *Ann. Rev. Biophys. Biomol. Struct.* 24:405). Cells are analyzed using an optical system that can measure spatial, as well as temporal dynamics. (Farkas et al. (993) *Ann. Rev. Physiol.* 55:785; Giuliano et al. (1990) In *Optical Microscopy for Biology*. B. Herman and K. Jacobson (eds.), pp. 543–557. Wiley-Liss, New York; Hahn et al (1992) *Nature* 359:736; Waggoner et al. (1996) *Hum. Pathol.* 27:494). The concept is to treat each cell as a "well" that has spatial and temporal information on the activities of the labeled constituents.

HCS can be performed on living or fixed cells, using a variety of labeled reporter molecules, such as antibodies, biological ligands, nucleic acid hybridization probes, and multicolor luminescent indicators and "biosensors." The choice of fixed or live cell screens depends on the specific cell-based assay required.

The results obtained from HCS provide more relevant information about a drug candidate's potential effect on cells than is available from genomic or proteomic methods, and can dramatically reduce costs in animal testing, while increasing the speed of new drug development.

While HCS can be combined on a single platform with high throughput screening (HTS) (see, for example, U.S. Pat. Nos. 5,989,835 and 6,103,479, as well as published PCT application no. WO 98/38490), methods that further increase the throughput capabilities of high content cell-based drug screening would be of great value to the art. The average "hit" rate (i.e.: detection of a positive response) in most viable high content cell-based screens ranges from 0.1% to 1.0% of compounds screened. Therefore, the vast majority of wells screened in a microplate format yield a negative response, necessitating the screening of a large number of wells to detect a response of interest, which significantly impacts the capacity requirements of such high content cell-based screening assays. Thus, methods that increase the capacity to provide high content information on the effect of a test compound on cellular events of interest, while maintaining the "hit" rate, would provide a tremendous increase in the utility of high content cell based screens.

SUMMARY OF THE INVENTION

The present invention fulfills the need in the art for methods to increase the capacity to provide high content information on the effect of a test compound on cellular events of interest, while maintaining the "hit" rate, and dramatically reduce the cost and time required to carry out high content cell-based screening, and is further applicable to methods for high throughput screening of a variety of biological targets.

In one aspect, methods are provided for increasing the throughput of high content cell based screening assays, comprising:

a) providing at least a first array of locations that contain multiple cells, wherein the cells comprise a first reporter set, wherein the first reporter set comprises at least a first fluorescent reporter molecule and a second fluorescent reporter molecule, wherein the fluorescent reporter molecules in the first reporter set
   i) report on different cellular events;
   ii) exhibit phenotypically similar behavior; and
   iii) emit fluorescence at wavelengths detectable in at least a first channel of a fluorescence detection device;

b) conducting a primary screen that comprises imaging the at least first array of locations in high content mode to obtain fluorescent signals in the first channel from the fluorescent reporter molecules in the first reporter set, wherein the imaging occurs either before, after, and/or simultaneously with contacting of the at least first array of locations with one or more test compounds;

c) detecting test compound induced changes in the fluorescent signals from the fluorescent reporter molecules in the first reporter set, wherein a test compound induced change in the fluorescent signals indicates an effect of the one or more test compounds on one or more cellular event(s) reported on by the fluorescent reporter molecules in the first reporter set; and d) deconvolving the test compound induced changes, wherein the deconvolving comprises conducting one or more secondary screens.

In a preferred embodiment, at least one of the secondary screens comprises a method selected from the group consisting of:

i) screening positive locations on the first array of locations in which test compound induced changes were detected in the primary screen, and optionally screening one or more control locations on the first array of locations, wherein the cells in the positive locations and any control locations to be screened in the secondary screen are further contacted with two or more further fluorescent reporter molecules that are optically distinguishable from each other and from the fluorescent reporter molecules in the first reporter set, wherein at least one of the further fluorescent reporter molecules reports on the same cellular event as the first fluorescent reporter molecule, and wherein at least one of the further fluorescent reporter molecules reports on the same cellular event as the second fluorescent reporter molecule; and ii) screening an at least second array of locations and an at least third array of locations that contain multiple cells, wherein the cells on the at least second array of locations comprise the first fluorescent reporter molecule and not the second fluorescent reporter molecule; and wherein the cells on the at least third array of locations comprise the second fluorescent reporter molecule and not the first fluorescent reporter molecule; wherein the deconvolving comprises contacting the at least second array of locations and the at least third array of locations with only those test compounds that produced test compound induced changes during the primary screen, and optionally with one or more control compounds.

In a further embodiment, the first reporter set comprises three or more fluorescent reporter molecules. In this embodiment, deconvolving can comprise either partially or completely deconvolving the effect of the one or more test compounds on the cellular events reported on by the fluorescent reporter molecules in the first reporter set.

In another embodiment, the cells further comprise at least a second reporter set, wherein the at least second reporter set comprises at least a third fluorescent reporter molecule and a fourth fluorescent reporter molecule, wherein the fluorescent reporter molecules in the second reporter set
  i) report on different cellular events;
  ii) exhibit phenotypically similar behavior; and
  iii) emit fluorescence at wavelengths detectable in at least a second channel of a fluorescence detection device;
wherein the primary screen further comprises imaging the at least first array of locations in high content mode to obtain fluorescent signals in the second channel from the fluorescent reporter molecules in the second reporter set; and wherein the detecting further comprises detecting test compound induced changes in the fluorescent signals from the fluorescent reporter molecules in the second reporter set, wherein test compound induced changes in the fluorescent signals from the fluorescent reporter molecules in the second reporter set indicate an effect of the one or more test compounds on one or more cellular events reported on by the at least second reporter set.

In this embodiment, deconvolving can comprise either partially or completely deconvolving the effect of the one or more test compounds on the cellular events reported on by the fluorescent reporter molecules in the first reporter set and the second reporter set.

BRIEF DESCRIPTION OF THE DRAWINGS

FIG. 1 is a schematic example of results obtained when using a single reporter set with four fluorescent reporter molecules, and deconvolving on a separate array of locations.

FIG. 2 is a schematic example of results obtained when using two reporter sets with two fluorescent reporter molecules in each reporter set, and deconvolving on a separate array of locations.

FIG. 4 is a schematic demonstration of potential timesaving, relative to standard high content cell-based screening, of an embodiment of the methods of the invention wherein the cells comprise a single reporter set consisting of 4 fluorescent reporter molecules.

DETAILED DESCRIPTION OF THE INVENTION

Figure 3:
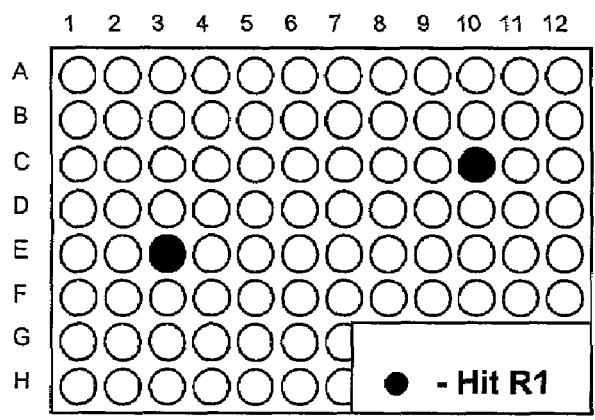
FIG. 3 is a schematic example of results obtained when using a single reporter set with 3 fluorescent reporter molecules, and partially deconvolving on the same array of locations as was used for the primary screen.

The present invention involves the pooling of multiple high content cell-based screening assays, and carrying out a primary screen in one or more channels of a fluorescence detection device, which drastically increases the number of simultaneous high content cell-based screening events that can be carried out. Subsequent deconvolution of primary screen "hits" (ie: those wells or locations on an array of locations in which the one or more test compounds caused a change in the fluorescence signal(s) from the fluorescent reporter molecules in the cells) enables much more rapid generation of high content cell screening data than was previously possible, and at significantly reduced costs.

In one aspect, the present invention provides methods for increasing the throughput of high content cell based screening assays, comprising:

a) providing at least a first array of locations that contain multiple cells, wherein the cells comprise a first reporter set, wherein the first reporter set comprises at least a first fluorescent reporter molecule and a second fluorescent reporter molecule, wherein the fluorescent reporter molecules in the first reporter set
  i) report on different cellular events;
  ii) exhibit phenotypically similar behavior; and
  iii) emit fluorescence at wavelengths detectable in at least a first channel of a fluorescence detection device;

b) conducting a primary screen that comprises imaging the at least first array of locations in high content mode to obtain fluorescent signals in the first channel from the fluorescent reporter molecules in the first reporter set, wherein the imaging occurs either before, after, and/or simultaneously with contacting of the at least first array of locations with one or more test compounds;

c) detecting test compound induced changes in the fluorescent signals from the fluorescent reporter molecules in the first reporter set, wherein a test compound induced change in the fluorescent signals indicates an effect of the one or more test compounds on one or more cellular event(s) reported on by the fluorescent reporter molecules in the first reporter set; and d) deconvolving the test compound induced changes, wherein the deconvolving comprises conducting one or more secondary screens.

In a preferred embodiment, at least one of the secondary screens comprises a method selected from the group consisting of:

i) screening positive locations on the first array of locations in which test compound induced changes were detected in the primary screen, and optionally screening one or more control locations on the first array of locations, wherein the cells in the positive locations and any control locations to be screened in the secondary screen are further contacted with two or more further fluorescent reporter molecules that are optically distinguishable from each other and from the fluorescent reporter molecules in the first reporter set, wherein at least one of the further fluorescent reporter molecules reports on the same cellular event as the first fluorescent reporter molecule, and wherein at least one of the further fluorescent reporter molecules reports on the same cellular event as the second fluorescent reporter molecule; and ii) screening an at least second array of locations and an at least third array of locations that contain multiple cells, wherein the cells on the at least second array of locations comprise the first fluorescent reporter molecule and not the second fluorescent reporter molecule; and wherein the cells on the at least third array of locations comprise the second fluorescent reporter molecule and not the first fluorescent reporter molecule; wherein the deconvolving comprises contacting the at least second array of locations and the at least third array of locations with only those test compounds that produced test compound induced changes during the primary screen, and optionally with one or more control compounds.

The use of deconvolution greatly decreases the time and expense of simultaneously identifying the effect of a given test compound or compounds on a number of different cellular events.

As used herein, an "array" includes any substrate, or portion of such a substrate, on which multiple locations of cells can be attached, including but not limited to microplates with any number of wells, slides, chambered slides, chemically or physically patterned substrates, and microwells on a microplate, as described in U.S. Pat. No. 6,103,479, incorporated by reference herein in its entirety. Thus, an array of locations could, for example, be a 96 well microplate, as is standard in the art; it could also be some subsection of a 96 well microplate, such as 1, 4, 8, 16, 32, or 48 wells on a 96 well microplate. Thus, in embodiments of the invention when more than one array of locations are used, recitation of a "second array of locations," etc., encompasses both the situation where the first and second array of locations (or second and third array of locations, etc.) are on different substrates, such as two separate microplates, and also encompasses the situation wherein the first array of locations is a one portion of a substrate, such as a microplate, while the second array of locations is a separate portion of the same microplate.

As used herein, the cells on an "array of locations" can comprise a homogenous population of cells with respect to reporter set, or can comprise multiple cell populations, wherein each cell population comprises a different reporter set, in order to further increase the capability of the high content screen.

As used herein, "control locations" can be locations without cells (for example, media plus one or more test compounds only), or locations with cells that have been treated in such a way as to provide a control for the interpretation of the assay results (for example, cells not treated with any test compound; cells treated with a control compound of some sort (such as a known activator or inhibitor of the cellular event being assayed), etc.).

As used herein, the phrase "the cells comprise a first reporter set" means that individual fluorescent reporter molecules may be expressed by transfected cells or added to the cells via non-mechanical modes including, but not limited to, diffusion, facilitated or active transport, signal-sequence-mediated transport, and endocytotic or pinocytotic uptake; or combinations thereof, at any time during the screening assay. Mechanical bulk loading methods, which are well known in the art, can also be used to load fluorescent probes into living cells (Barber et al. (1996), *Neuroscience Letters* 207:17–20; Bright et al. (1996), *Cytometry* 24:226–233; McNeil (1989) in *Methods in Cell Biology*, Vol. 29, Taylor and Wang (eds.), pp. 153–173). These methods include, but are not limited to, electroporation and other mechanical methods such as scrape-loading, bead-loading, impact-loading, syringe-loading, hypertonic and hypotonic loading. Additionally, cells can be genetically engineered to express fluorescent reporter molecules, such as green fluorescent protein (GFP), coupled to a protein of interest (Chalfie and Prasher U.S. Pat. No. 5,491,084; Cubitt et al. (1995), *Trends in Biochemical Science* 20:448–455). Fluorescently labe high degree of specificity for attaching to a single molecular target in a mixture of molecules as complex as a cell. The fluorescent reporter molecules that a given cell possesses may all be introduced to the cells via the same technique, or via any combination of such techniques.

There is a continually growing family of fluorescent reagents that are used to measure the temporal and spatial distribution, content, and activity of intracellular ions, metabolites, macromolecules, and organelles. Classes of these fluorescent reporter molecules include, but are not limited to, fluorescently labeled biomolecules, such as proteins, phospholipids, nucleic acid hybridizing probes, antibodies, and small molecules. Once in the cell, the fluorescent reporter molecules accumulate at their target domain as a result of specific and high affinity interactions with the target domain (either directly or indirectly, through another molecule) or other modes of molecular targeting such as signal-sequence-mediated transport.

As used herein, "changes" in the fluorescent signals that are detected include, but are not limited to, the broad classes of changes in fluorescence intensity, changes in fluorescence spatial distribution, and spectral shifting. Changes in fluorescence intensity include, but are not limited to, increase or decrease of fluorescence intensity, and changes in the ratio of fluorescence intensity relative to a control sample, a different cellular compartment, or relative to the same cell at different time points. Changes in fluorescence spatial distribution include any redistribution in the cell, or changes in distribution ratios of the fluorescent reporter molecules, either between different cellular compartments in the same cell at different time points, or relative to a control sample. "Spectral shifting" means a change in the fluorescence emission profile of a fluorescent reporter molecule including but not limited to changes occurring as a result of fluorescent resonance energy transfer (FRET) and fluorescence lifetime measurements (FLM).

As used herein, the term "reporter set" means two or more fluorescent reporter molecules that
   i) report on different cellular events;
   ii) exhibit phenotypically similar behavior; and
   iii) emit fluorescence at wavelengths detectable in at least a first channel of a fluorescence detection device.

As used herein, the term "cellular event" means a cellular response that can be reported on by a detectable reporter molecule, such as a fluorescent reporter molecule. Non-limiting examples of such cellular responses include, but are not limited to, translocation of a cellular factor (including, but not limited to, proteins, nucleic acids, and lipids) between one part of the cell and another (including, but not limited to, between organelles and other specialized cell structures, such as between cytoplasm-nucleus, cytoplasm-cell membrane, cell membrane-nucleus, endoplasmic reticulum-golgi, organelles and cellular polymeric networks, such as microtubules, intermediate filaments, and actin filaments, etc.), changes in the mass of a cell structure (including but not limited to organelles, polymeric networks, such as microtubules, intermediate filaments, and actin filaments), changes in the structural characteristics of a cell structure (including but not limited to changes in the degree of polymerization of a cell structure; changes in the integrity of a cell structure, etc.), changes in the activity of a cellular factor (including but not limited to enzymatic activation, expression, and other modifications), and changes in environment of a reporter molecule (including, but not limited to, changes in pH environment, ionic environment ($Ca^{++}$, $K^+$, $Na^+$, etc.), and lipid environment). The fluorescent reporter molecule can directly report on the cellular event (for example, a primary antibody binding to a transcription factor that is being assayed for translocation from the cytoplasm to the nucleus), or may indirectly report on the cellular event (for example, a secondary antibody binding to the antibody binding to a transcription factor that is being assayed for translocation from the cytoplasm to the nucleus).

"Different" cellular events refer to non-identical events. Thus, two fluorescent reporter molecules that each report on translocation of c-jun from the cytoplasm to the nucleus do not report on "different cellular events", while if one fluorescent reporter molecule reports on c-jun translocation from the cytoplasm to the nucleus, while a second fluorescent reporter molecule reports on translocation of c-fos from the cytoplasm to the nucleus, then the two reporters report on different cellular events. Alternatively, the second fluorescent reporter molecule may report on viral infection, so long as it and the first fluorescent reporter molecule exhibit phenotypically similar behavior in the cell, as defined below. Thus, more than one specific cellular event is being reported on by each reporter set, providing for parallel analysis of multiple cellular events in a single primary screen. As discussed further below, the cells may comprise more than one reporter set, and each reporter set may comprise any number of such different fluorescent reporter molecules, so long as they fulfill the further requirements set out below.

That two or more fluorescent reporter molecules in a single reporter set exhibit "phenotypically similar behavior" in the cell means that the two or more fluorescent reporter molecules occupy a similar space in the cell (for example, they are each predominately non-nuclear and cytoplasmic) and move in a similar way in the cell (for example, upon activation they predominately move to the nucleus), so that they can be analyzed simultaneously by an appropriate image analysis method. For example, a first fluorescent reporter molecule reports on c-jun activation by translocating from the cytoplasm to the nucleus upon activation, while a second fluorescent reporter molecule reports on viral infection by translocating from the cytoplasm to the nucleus upon viral infection. Since both fluorescent reporter molecules move from the cytoplasm to the nucleus upon appropriate stimulation, they exhibit "phenotypically similar behavior", and can be simultaneously analyzed by an image analysis method that measures translocation of a fluorescent reporter molecule between the cytoplasm and nucleus of the cells. One of skill in the art will recognize that similar reporter sets of phenotypically similar fluorescent reporter molecules (including those with more than two fluorescent reporter molecules) can be designed for any type of translocation, mass detection, structural characteristic detection, and environment sensing, as discussed in more detail below.

As used herein, "emit fluorescence at wavelengths detectable in at least a first channel of a fluorescence detection device" means that the different fluorescent reporter molecules in the first reporter set emit fluorescence within the wavelength cut-off range of the filter set used to collect fluorescence for a particular channel. One or more of the reporters in a single reporter set may also emit fluorescence outside the wavelength cut-off range, so long as it does significantly not bleed through (contaminate) other channels that are also being used to measure fluorescence either from fluorescent reporter molecules in other reporter sets, or from other fluorescence reporters used to deconvolve the results of the primary screen or to identify specific cellular structures for the purposes of specific high content screening assays (such as the use of a nuclear stain to identify individual cells, when so desired). This phrase does not mean that the fluorescent reporter molecules in the first reporter set do not emit fluorescence outside of the first channel cut-off.

In another embodiment, the cells further comprise at least a second reporter set, wherein the at least second reporter set comprises at least a third fluorescent reporter molecule and a fourth fluorescent reporter molecule, wherein the fluorescent reporter molecules in the second reporter set
   i) report on different cellular events;
   ii) exhibit phenotypically similar behavior; and
   iii) emit fluorescence at wavelengths detectable in at least a second channel of a fluorescence detection device;
   wherein the primary screen further comprises imaging the at least first array of locations in high content mode to obtain fluorescent signals in the second channel from the fluorescent reporter molecules in the second reporter set; and
   wherein the detecting further comprises detecting test compound induced changes in the fluorescent signals from the fluorescent reporter molecules in the second reporter set, wherein test compound induced changes in the fluorescent signals from the fluorescent reporter molecules in the second reporter set indicate an effect of the one or more test compounds on one or more cellular event(s) reported on by the at least second reporter set.

Thus, when multiple reporter sets are used, each reporter set is imaged in a different channel of the fluorescence detection device. Thus, the fluorescent reporter molecules in the first reporter set must be "optically distinguishable" from the fluorescent reporter molecules in the second reporter set. As used herein, "optically distinguishable" or "spectrally distinguishable" means that fluorescent signals from more than one fluorescent reporter molecule are distinguishable from each other. Preferably, the optically distinguishable reporter molecules do not emit fluorescence at overlapping wavelengths. However, where a first fluorescent reporter molecule has overlapping wavelengths of fluorescence emission with a second fluorescent reporter molecule, such overlapping is acceptable, so long as the fluorescent signals from the first fluorescent reporter molecule do not obscure the detectable signals from the second fluorescent reporter molecule in the channel for detecting fluorescence emission from the second fluorescent reporter molecule.

In a preferred embodiment, each reporter set emits fluorescence at wavelengths not detectable in the channel used to image the fluorescent signals from the other reporter set. Any number of different reporter sets can be used in the methods of the present invention, so long as the fluorescence emission from the different sets can be imaged in separate, non-overlapping channels as described above.

In a preferred embodiment, reporter sets are designed to analyze several parts of a cellular pathway with the same reporter set, so that a "hit" could identify a pathway affected by the test compound, and deconvolution can be used to identify the step in the pathway that the test compound affected.

As used herein, "imaging . . . in high content mode" means detection of fluorescence signals at subcellular resolution, wherein the cellular localization of the fluorescence signals is determined. Such a high content mode image comprises a digital representation of the fluorescent signals from the fluorescent reporter molecules, and does not require a specific arrangement or display of the digital representation. In preferred embodiments, well known formats for such "images" are employed, including but not limited to .dib, .tiff, .jpg, .bmp. In further preferred embodiments, the images are analyzed algorithmically, and/or displayed to provide a visual representation of the image.

The one or more test compounds can be of any nature, including, but not limited to, chemical and biological compounds and environmental samples. The one or more test compounds may also comprise a plurality of compounds, including but not limited to combinatorial chemical libraries and natural compound libraries. Contacting of the cells with the one or more test compounds can occur before, after, and/or simultaneously with imaging of the cells, depending on the assay design. For example, in order to carry out kinetic screening, it is necessary to image the cells at multiple time points, and the user may acquire such images before, at the time of, and after contacting of the cells with the test compound.

As used herein, the term "primary screen" refers to the screen in which the cumulative response to the test compound of all of the fluorescent reporter molecules in the reporter sets are determined, with no distinction being made as to the relative contribution of any of the individual fluorescent reporter molecule responses.

Thus, the cumulative effect of the one or more test compounds on all of the fluorescent reporter molecules in the reporter sets is determined in the primary screen. In some cases, no further screening is necessary. For example, such information is particularly useful where it is desired to determine if a test compound produces a given phenotypic event, but it is not necessary to identify the specific cellular event that the test compound acts on. In one non-limiting example, if it was desired to identify a test compound that affected a specific cell signaling pathway, then one could design a reporter set consisting of three fluorescent reporter molecules that reported on activation of three different transcription factors in the specific cell signaling pathway, wherein activation of the signaling pathway induced translocation of one or more of the transcription factors to the nucleus from the cytoplasm. Upon contact with an activating test compound, the array of locations would be imaged to identify translocation of fluorescent signals from the cytoplasm to the nucleus, and an activator of the specific cell signaling pathway would thus be identified.

As used herein, the term "deconvolve" or "deconvolving" means performing one or more secondary assays to determine which of the individual fluorescent reporter molecules in a reporter set were affected by the one or more test compounds that produced an effect in the primary screen (the "active test compound(s)"). Deconvolving can be carried out on the same array of locations as the primary screen, or can be carried out on one or more array(s) of locations other than the at least first array of locations on which the primary screen was conducted. In either case, control locations and control test compounds can optionally be employed.

When individual wells on the at least first array of locations are contacted with more than one test compound, deconvolving can also comprise a two dimensional deconvolution, comprising deconvolving the effects of each individual test compound used to contact positive locations on the primary screen, as well as determining which of the individual fluorescent reporter molecules in a reporter set were affected by the test compounds in the primary screen.

If deconvolving is carried out on fixed cells and on the same array of locations as the primary screen, then it is not required to contact the cells again with the one or more test compounds that were active in the primary screen. If deconvolving is carried out on live cells and on the same array of locations as the primary screen, then it may be necessary to contact the cells again with the one or more test compounds that were active in the primary screen, depending on the amount of time elapsed between the primary screen and the secondary screen(s), as well as the duration of the response assayed in the primary screen. If deconvolving is carried out on a different array of locations than the primary screen, it is necessary to contact the cells to be screened in the secondary screen(s) with the one or more test compounds that were active in the primary screen.

Deconvolution can be carried out in many ways, including but not limited to:

1. Complete deconvolution completely separates the effect of the one or more test compounds on each of the cellular events reported on by the fluorescent reporter molecules in the primary screen.

a. All secondary screens carried out on new arrays of locations: A separate array of locations containing cells is provided for each fluorescent reporter molecule in a reporter set, wherein the cells in each individual array of locations possesses only one of the fluorescent reporter molecules from a given reporter set. For example, if in the primary screen the cells possess three fluorescent reporter molecules (A, B, and C) in a single reporter set, then in the secondary screen, three different arrays of locations (1, 2, and 3) are used, each array of locations containing cells with only one of the reporters (For example, cells on array of locations 1 possess reporter A, cells on array of locations 2 possess reporter B, and cells on array of locations 3 possess reporter C). Thus, a different secondary screen is conducted, and different images are obtained, for each fluorescent reporter molecule, with all screens being carried out on different arrays of locations than the one on which the primary screen was conducted.

For example, one embodiment of complete deconvolving using all secondary screens carried out on separate arrays of locations from the primary screen, when the cells possess a single reporter set of two fluorescent reporter molecules, comprises:

A) providing at least a second array of locations that contain multiple cells, wherein the cells on the at least second array of locations comprise the first fluorescent reporter molecule and not the second fluorescent reporter molecule;

B) providing at least a third array of locations that contain multiple cells, wherein the cells on the at least third array of locations comprise the second fluorescent reporter molecule and not the first fluorescent reporter molecule;

C) imaging the at least second array of locations and the at least third array of locations in high content mode to obtain fluorescent signals from the first fluorescent reporter molecule on the at least second array of locations and fluorescent signals from the second fluorescent reporter molecule on the at least third array of locations, wherein the imaging occurs either before, after, and/or simultaneously with contacting of the at least second array of locations and the at least third array of locations with one or more active test compounds that produced test compound induced changes during the primary screen, and optionally with one or more control compounds; and D) detecting active test compound induced changes in the fluorescent signals from the first fluorescent reporter molecule on at least second array of locations and/or the fluorescent signals from the second fluorescent reporter molecule on the at least third array of locations, wherein an active test compound induced change in the fluorescent signals from the first fluorescent reporter molecule on the at least second array of locations indicates an effect of the one or more active test compounds on the cellular event reported on by the first fluorescent reporter molecule, and wherein an active test compound induced change in the fluorescent signals from the second fluorescent reporter molecule on the at least third array of locations indicates an effect of the one or more active test compounds on the cellular event reported on by the second fluorescent reporter molecule.

If the cells possess a single reporter set of three different fluorescent reporter molecules, one embodiment of complete deconvolution on new arrays of locations comprises:

A) providing at least a second array of locations that contain multiple cells, wherein the cells on the at least second array of locations comprise the first fluorescent reporter molecule and not the second fluorescent reporter molecule or the third fluorescent reporter molecule;

B) providing at least a third array of locations that contain multiple cells, wherein the cells on the at least third array of locations comprise the second fluorescent reporter molecule and not the first fluorescent reporter molecule or the third fluorescent reporter molecule;

C) providing at least a fourth array of locations that contain multiple cells, wherein the cells on the at least fourth array of locations comprise the third fluorescent reporter molecule and not the first fluorescent reporter molecule or the second fluorescent reporter molecule;

D) imaging the at least second array of locations, the at least third array of locations, and the at least fourth array of locations in high content mode to obtain fluorescent signals from the first fluorescent reporter molecule on the at least second array of locations, fluorescent signals from the second fluorescent reporter molecule on the at least third array of locations, and fluorescent signals from the third fluorescent reporter molecule on the at least fourth array of locations, wherein the imaging occurs either before, after, and/or simultaneously with contacting of the at least second array of locations, the at least third array of locations, and the at least fourth array of locations with one or more active test compounds that produced test compound induced changes during the primary screen, and optionally with one or more controls; and E) detecting active test compound induced changes in the fluorescent signals from the first fluorescent reporter molecule on the at least second array of locations, the second fluorescent reporter molecule on the at least third array of locations, and/or the third fluorescent reporter molecule on the at least fourth array of locations, wherein an active test compound induced change in the fluorescent signals from the first fluorescent reporter molecule on the at least second array of locations indicates an effect of the one or more active test compounds on the cellular event reported on by the first fluorescent reporter molecule, wherein an active test compound induced change in the fluorescent signals from the second fluorescent reporter molecule on the at least third array of locations indicates an effect of the one or more active test compounds on the cellular event reported on by the second fluorescent reporter molecule, and wherein an active test compound induced change in the fluorescent signals from the third fluorescent reporter molecule on the at least fourth array of locations indicates an effect of the one or more active test compounds on the cellular event reported on by the third fluorescent reporter molecule.

An example of complete deconvolution on a separate array of locations when the cells comprise a single reporter set of 4 fluorescent reporter molecules (F1–F4) is shown in FIG. 1. The primary screen is conducted in this example on a 96 well plate (the first array of locations), with a hit at location D4. The test compound or compounds used at location D4 in the primary screen is/are then used to screen separate arrays of locations, wherein the cells in any location comprise only one of F1–F4 (or none, such as in optional control wells). The cells in each well are different with respect to fluorescent reporter molecule, and thus each well constitutes a separate "array of locations". In this example, four separate arrays of locations are used, wherein each array of locations consists of a single well, and each array of locations is on a single microplate. If the primary screen had yielded two hits, then the secondary screening would have involved 2 different wells for each cell type (ie: two F1 wells, each with one of the two compounds that were identified as hits, etc.) In this case, there would still have been four arrays of locations, with each array consisting of two wells (e.g.: the two F1 wells make up a second array of locations, etc.)

If the cells possess two reporter sets of two different fluorescent reporter molecules, one embodiment of complete deconvolution on new arrays of locations comprises:

A) providing at least a second array of locations that contain multiple cells, wherein the cells on the at least second array of locations comprise the first fluorescent reporter molecule and not the second fluorescent reporter molecule, the third fluorescent reporter molecule, or the fourth fluorescent reporter molecule;

B) providing at least a third array of locations that contain multiple cells, wherein the cells on the at least third array of locations comprise the second fluorescent reporter molecule and not the first fluorescent reporter molecule, the third fluorescent reporter molecule, or the fourth fluorescent reporter molecule;

C) providing at least a fourth array of locations that contain multiple cells, wherein the cells on the at least fourth array of locations comprise the third fluorescent reporter molecule and not the first fluorescent reporter molecule, the second fluorescent reporter molecule, or the fourth fluorescent reporter molecule;

D) providing at least a fifth array of locations that contain multiple cells, wherein the cells on the at least fifth array of locations comprise the fourth fluorescent reporter molecule and not the first fluorescent reporter molecule, the second fluorescent reporter molecule, or the third fluorescent reporter molecule;

E) imaging the at least second array of locations, the at least third array of locations, the at least fourth array of locations, and the at least fifth array of locations in high content mode to obtain fluorescent signals from the first fluorescent reporter molecule on the at least second array of locations, fluorescent signals from the second fluorescent reporter molecule on the at least third array of locations, fluorescent signals from the third fluorescent reporter molecule on the at least fourth array of locations, and fluorescent signals from the fourth fluorescent reporter molecule on the at least fifth array of locations, wherein the imaging occurs either before, after, and/or simultaneously with contacting of the at least second array of locations, the at least third array of locations, the at least fourth array of locations, and the at least fifth array of locations with one or more active test compounds that produced test compound induced changes during the primary screen, and optionally with one or more control compounds; and F) detecting active test compound induced changes in the fluorescent signals from the first fluorescent reporter molecule on the at least second array of locations, the second fluorescent reporter molecule on the at least third array of locations, the third fluorescent reporter molecule on the at least fourth array of locations, and/or the fourth fluorescent reporter molecule on the at least fifth array of locations, wherein an active test compound induced change in the fluorescent signals from the first fluorescent reporter molecule on the at least second array of locations indicates an effect of the one or more active test compounds on the cellular event reported on by the first fluorescent reporter molecule, wherein an active test compound induced change in the fluorescent signals from the second fluorescent reporter molecule on the at least third array of locations indicates an effect of the one or more active test compounds on the cellular event reported on by the second fluorescent reporter molecule, wherein an active test compound induced change in the fluorescent signals from the third fluorescent reporter molecule on the at least fourth array of locations indicates an effect of the one or more active test compounds on the cellular event reported on by the third fluorescent reporter molecule, and wherein an active test compound induced change in the fluorescent signals from the fourth fluorescent reporter molecule on the at least fifth array of locations indicates an effect of the one or more active test compounds on the cellular event reported on by the fourth fluorescent reporter molecule.

Similar deconvolving methods can be designed for any number of reporter sets with any number of fluorescent reporter molecules in a reporter set, based on appropriate selection of fluorescent reporter molecules and filter sets, as described above.

b. all secondary screens carried out on same array of locations as the primary screen: In this embodiment, a second round of screening on the same array is conducted, thus necessitating that one be able to distinguish the results of the primary screen from the results of the secondary screen. For example, if the primary screen utilized an array with cells that had been contacted with fluorescent reporter molecules comprising antibodies A, B, and C, where A was produced in sheep, B was produced in rabbits, and C was produced in mice, then the secondary screen could involve contacting the same cells with three new fluorescent reporter molecules comprising antibodies D, E, and F, where D specifically recognized sheep antibodies, E specifically recognized rabbit antibodies, and F specifically recognized mouse antibodies, and wherein D, E, and F were spectrally distinguishable. Alternatively, some type of specific tertiary staining that would yield spectrally distinguishable fluorescent reporter molecules D, E, and F can be used. Thus, on a single array, one could carry out both the primary and the secondary screens, further increasing the speed and efficiency of the method.

For example, one embodiment of complete deconvolving using all secondary screens carried out on the same array of locations as the primary screen, when the cells possess a single reporter set of two fluorescent reporter molecules, comprises:

A) contacting the cells in only positive locations on the at least first array of locations in which a test compound induced change was detected, and optionally control locations, with at least a third fluorescent reporter molecule and a fourth fluorescent reporter molecule, wherein the third fluorescent reporter and the fourth fluorescent molecule are optically distinguishable from each other and from the first fluorescent reporter molecule and the second fluorescent reporter molecule, and wherein the third fluorescent reporter molecule reports on the same cellular event as the first fluorescent reporter molecule, and wherein the fourth fluorescent reporter molecule reports on the same cellular event as the second fluorescent reporter molecule;

B) imaging the positive locations on the at least first array of locations, and optionally control locations, in high content mode to obtain fluorescent signals from the third fluorescent reporter molecule and the fourth fluorescent reporter molecule; and C) detecting active test compound induced changes in the fluorescent signals from the third fluorescent reporter molecule and/or the fluorescent signals from the fourth fluorescent reporter molecule, wherein an active test compound induced change in the fluorescent signals from the third fluorescent reporter molecule indicates an effect of the one or more active test compounds on the cellular event reported on by the first fluorescent reporter molecule, and wherein an active test compound induced change in the fluorescent signals from the at least fourth fluorescent reporter molecule indicates an effect of the one or more active test compounds on the cellular event reported on by the second fluorescent reporter molecule.

If the cells possess a single reporter set of three different fluorescent reporter molecules, one embodiment of complete deconvolution on the same array of locations as the primary screen comprises:

A) contacting the cells in only positive locations on the at least first array of locations in which a test compound induced change was detected, and optionally control locations, with at least a fourth fluorescent reporter molecule, a fifth fluorescent reporter molecule, and a sixth fluorescent reporter molecule, wherein the fourth fluorescent reporter molecule, the fifth fluorescent reporter molecule, and the sixth fluorescent reporter molecule are optically distinguishable from each other and from the fluorescent reporter molecules in the first reporter set, and wherein the fourth fluorescent reporter molecule reports on the same cellular event as the first fluorescent reporter molecule, wherein the fifth fluorescent reporter molecule reports on the same cellular event as the second fluorescent reporter molecule, and wherein the sixth fluorescent reporter molecule reports on the same cellular event as the third fluorescent reporter molecule;

B) imaging the positive locations on the at least first array of locations, and optionally control locations, in high content mode to obtain fluorescent signals from the fourth fluorescent reporter molecule, the fifth fluorescent reporter molecule, and the sixth fluorescent reporter molecule; and C) detecting active test compound induced changes in the fluorescent signals from the fourth fluorescent reporter molecule, the fluorescent signals from the fifth fluorescent reporter molecule, and/or the fluorescent signals from the sixth fluorescent reporter molecule, wherein an active test compound induced change in the fluorescent signals from the fourth fluorescent reporter molecule indicates an effect of the one or more active test compounds on the cellular event reported on by the first fluorescent reporter molecule, wherein an active test compound induced change in the fluorescent signals from the fifth fluorescent reporter molecule indicates an effect of the one or more active test compounds on the cellular event reported on by the second fluorescent reporter molecule, and wherein an active test compound induced change in the fluorescent signals from the sixth fluorescent reporter molecule indicates an effect of the one or more active test compounds on the cellular event reported on by the third fluorescent reporter molecule.

If the cells possess two reporter sets of two different fluorescent reporter molecules each, one embodiment of complete deconvolution on the same array of locations as the primary screen comprises:

A) contacting the cells in only positive locations on the at least first array of locations in which a test compound induced change was detected, and optionally control locations, with at least a fifth fluorescent reporter molecule, a sixth fluorescent reporter molecule, a seventh fluorescent reporter molecule, and an eighth fluorescent reporter molecule, wherein the fifth fluorescent reporter molecule, the sixth fluorescent molecule, the seventh fluorescent molecule, and the eighth fluorescent molecule are optically distinguishable from each other and from the fluorescent reporter molecules in the first reporter set and the second reporter set, and wherein the fifth fluorescent reporter molecule reports on the same cellular event as the first fluorescent reporter molecule, the sixth fluorescent molecule reports on the same cellular event as the second fluorescent molecule, the seventh fluorescent molecule reports on the same cellular event as the third fluorescent molecule, and wherein the eighth fluorescent reporter molecule reports on the same cellular event as the fourth fluorescent reporter molecule;

B) imaging the positive locations on the at least first array of locations, and optionally control locations, in high content mode to obtain fluorescent signals from the fifth fluorescent reporter molecule, the sixth fluorescent reporter molecule, the seventh fluorescent reporter molecule, and the eighth fluorescent reporter molecule; and C) detecting active test compound induced changes in the fluorescent signals from the fifth fluorescent reporter molecule, the sixth fluorescent reporter molecule, the seventh fluorescent reporter molecule, and/or the eighth fluorescent reporter molecule, wherein an active test compound induced change in the fluorescent signals from the fifth fluorescent reporter molecule indicates an effect of the one or more active test compounds on the cellular event reported on by the first fluorescent reporter molecule, wherein an active test compound induced change in the fluorescent signals from the sixth fluorescent reporter molecule indicates an effect of the one or more active test compounds on the cellular event reported on by the second fluorescent reporter molecule, wherein an active test compound induced change in the fluorescent signals from the seventh fluorescent reporter molecule indicates an effect of the one or more active test compounds on the cellular event reported on by the third fluorescent reporter molecule, and wherein an active test compound induced change in the fluorescent signals from the eighth fluorescent reporter molecule indicates an effect of the one or more active test compounds on the cellular event reported on by the fourth fluorescent reporter molecule.

Similar deconvolving methods can be designed for any number of reporter sets with any number of fluorescent reporter molecules in a reporter set, based on appropriate selection of fluorescent reporter molecules and filter sets, as described above.

c. Some secondary screen carried out on new arrays, some on same array as for primary screen: Combination of the above methods.

2. Partial deconvolution separates the effect of the one or more test compounds on some of the cellular events reported on by the fluorescent reporter molecules. Partial deconvolution is preferred when one is attempting to identify a test compound or compounds that activate a given specific cellular response, and not related cellular responses, and data on the response for each individual fluorescent reporter molecules is not required. For example, if one wanted to identify a test compound that specifically activated c-jun translocation from the cytoplasm to the nucleus, but which did not activate c-fos or Nf-kB translocation to the nucleus, partial deconvolution (i.e.: separating out c-jun in a secondary screen, while combining c-fos and Nf-kB in a single secondary screen) could be used instead of full deconvolution, to further minimize time and reagent usage, and to provide information on the specificity of the test compound or compounds. Alternatively, if the cells screened comprise both a first and a second reporter set, and the primary screen detects a test compound that produced a change in the fluorescent signals only from the first reporter set, than it would be unnecessary to deconvolve the effects of the test compound on the second reporter set.

Thus, in one embodiment, partial deconvolving comprises deconvolving the effect of the one or more active test compounds on the cellular events reported on by the fluorescent reporter molecules in only one of the first reporter set and the at least second reporter set. As for complete deconvolving, partial deconvolving can be performed on the same array of locations as the primary screening, or can be carried out on one or more different array(s) of locations, or combinations thereof.

Partial deconvolution can be carried out in multiple ways, including but not limited to:

a. all secondary screens carried out on new arrays of locations: At least one of the new arrays for the secondary screen contains cells that possess more than one of the fluorescent reporter molecules in a reporter set, while the other new arrays contain cells that possess only one of the fluorescent reporter molecules. For example, if the primary screen utilized cells possessing fluorescent reporter molecules A, B, C, and D in a single reporter set, then the secondary screen could be carried out on two new arrays of locations (For example, Array of locations 1 with cells possessing A and B and Array of locations 2 with cells possessing C and D; or Array of locations 1 with cells possessing A, B, and C and Array of locations 2 with cells possessing D) or three new arrays (For example, Array of locations 1 with cells possessing A, Array of locations 2 with cells possessing B, and Array of locations 3 with cells possessing C and D). One of skill in the art will recognize that many such permutations of secondary screens can be designed.

FIG. 2 provides one example of this embodiment. Reporter set 1 (R1) consists of fluorescent reporter molecules F1 and F2, while reporter set 2 (R2) consists of fluorescent reporter molecules F3 and F4. All cells on the array of locations for the primary screen contain F1, F2, F3, and F4. The primary screen resulted in hits for R1 at location B2, for R2 at location D3, and for both R1 and R2 at location G2. In this example, both partial and complete deconvolution are used. Deconvolution comprises a secondary screen in which the test compound or compounds used at location B2 in the primary screen is/are then used to screen a separate array of locations (a second array of locations), wherein the cells in the second array comprise F1 and not F2, F3, or F4; a third array of locations, wherein the cells in the third array comprise F2 and not F1, F3, or F4; this secondary screen does not require screening for F3 or F4 (partial deconvolution), since the primary screen was not a hit relative to R2 at position B2. The test compound or compounds used at location D3 in the primary screen is/are then used to screen a separate array of locations (a fourth array of locations), wherein the cells in the fourth array comprise F3 and not F1, F2, or F4, and a fifth array of locations, wherein the cells in the fifth array comprise F4 and not F1, F2, or F3; this secondary screen does not require screening for F1 or F2 (partial deconvolution). The test compound or compounds used at location G2 in the primary screen is/are then used to screen the second, third, fourth, and fifth array of locations (complete deconvolution).

To deconvolve the entire plate, 4 separate arrays of locations on a single microplate are used: wells with cells containing F1 only (2 wells); wells with cells containing F2 only (2 wells); wells with cells containing F3 only (2 wells); and wells with cells containing F4 only (2 wells). As will be apparent to one of skill in the art, the arrangement of the wells that constitute an "array of locations" in these secondary screens is not critical.

b. one or more, but not all, of the secondary screens are carried out on a new array of locations: In this embodiment, one or more, but not all, of the secondary screens are carried out on the same array of locations as the primary screen. For example, where the array of locations for the primary screen includes cells with fluorescent reporter molecules A, B, and C, a set of secondary screens could comprise two new arrays of locations, one with cells possessing only A and one with cells possessing only B, while the results of the primary screen, compared to the results of the secondary screens for A and B, are used to determine the effect of the test compound on C. Thus, a new image is obtained in the secondary screen only for A and B, not for C. One of skill in the art will recognize that many such permutations of secondary screens can be designed.

c. all secondary screens carried out on same array of locations as the primary screen: Utilizing the same type of method as described above for complete deconvolution, type b, one could screen any array of locations comprising cells that possess fluorescent reporter molecules A, B, and C, where A and B comprise antibodies made in mice and C comprises an antibody made in rabbit. The same array would then be used for the secondary screen, when fluorescent reporter molecule D specific for mouse antibodies and fluorescent reporter molecule E specific for rabbit antibodies could also be used, wherein D and E are spectrally distinguishable. Alternatively, antibodies A and B could be produced in rabbit and C in mouse and used in the primary screen, while in the secondary screen antibody D could recognize rabbit antibodies, while antibody E could recognize mouse antibodies. One of skill in the art will recognize that many such permutations of secondary screens can be designed.

One example of this embodiment is shown in FIG. 3. The primary screen comprises the use of cells comprising a single reporter set (R1) of 3 fluorescent reporter molecules (F1–F3). Primary screening resulted in a hits at locations C10 and E3. Deconvolution then comprises contacting locations C10 and E3 with a fourth fluorescent reporter molecule (F4) that reports on the same cellular event as F1, and a fifth fluorescent reporter molecule (F5) that reports on the same cellular event as F2, wherein F4 and F5 are optically distinguishable from each other and from F1–F3. A hit for F4 in the secondary screen means that the one or more test compounds effect the cellular event reported on by F1; a hit for F5 in the secondary screen means that the one or more test compounds effect the cellular event reported on by F2; and no hit for either F4 or F5 in the secondary screen means that the one or more test compounds effect the cellular event reported on by F3.

The use of deconvolution greatly decreases the time and expense of simultaneously identifying the effect of a given test compound or compounds on a number of different cellular events. FIG. 4 is a schematic of potential time savings from using the methods of the invention, assuming a hit rate of 0.1 to 1.0% of the compounds tested. Using traditional high content cell-based screening, conducting 4 separate screens each with one fluorescent reporter molecule reporting on a cellular event of interest, each against a 10 microplate compound library requires screening of 40 plates. With an average processing time of one hour per microplate, the 4 screens require a total processing time of 40 hours.

In contrast, by using the methods of the invention, this time can be dramatically reduced. In one non-limiting example, by conducting a single primary screen using a single reporter set, as defined herein, containing the same 4 fluorescent reporter molecules reporting on different cellular events, on a 10 microplate compound library, and then deconvolving the primary screen on two plates, only 12 plates are required, and thus the total screening time is 12 hours. This represents a 70% decrease in the screening time required for a 10 plate compound library. Greater reductions in time compared to standard high content cell-based screening can be achieved for larger jobs, or by using variations of the deconvolution methods disclosed herein.

Furthermore, the use of fewer plates means the use of less reagents and drug candidates, which can dramatically decrease the cost of test compound screening and the use of scarce reagents.

The cells being screened may also comprise fluorescent markers that can be used to identify specific cell structures for various purposes. For example, the cells may be contacted with a nuclear stain, such as Hoechst 33342, for the purpose of identifying individual cells. Similarly, fluorescent markers may be used to create masks of specific cellular regions, in order to measure fluorescent signals from the fluorescent reporter molecules in the reporter set(s) within the mask(s). Such fluorescent markers may in some assays be one of the fluorescent reporter molecules in a reporter set, or alternatively may be used to add functionality to the high content cell-based screening assay.

As used herein, "fluorescence detection device" means a device capable of carrying out the imaging required to carry out the invention, including, but not limited to, fluorescence microscopes; light scanning microscopy systems, including but not limited to point scanning, spinning disk, confocal, line scanning, and multi-photon microscopy systems; and epifluorescence microscopes. In a preferred embodiment, a fluorescence microscope is used as part of an automated cell screening system, which further comprises a fluorescence optical system with a stage adapted for holding cells and a means for moving the stage, a digital camera, a light source, and a computer for receiving and processing the digital data from the digital camera, as well as for storing and displaying the data.

The methods of the invention may be used to identify agonists or antagonists of a given cellular event.

In a further aspect, the present invention provides computer readable storage media, for automatically carrying out the methods of the invention on a fluorescence detection device. As used herein the term "computer readable medium" includes magnetic disks, optical disks, organic memory, and any other volatile (e.g., Random Access Memory ("RAM")) or non-volatile (e.g., Read-Only Memory ("ROM")) mass storage system readable by the CPU. The computer readable medium includes cooperating or interconnected computer readable medium, which exist exclusively on the processing system or be distributed among multiple interconnected processing systems that may be local or remote to the processing system.

The present invention is not limited to the field of high content cell-based screening. For example, the same methods can be used for high throughput screening of cells, as well as screening of other biological targets, such as tissue sections, cell extracts, protein extracts, isolated proteins, and isolated nucleic acids, that comprise the recited reporter sets, wherein the cellular events are instead "biological events," such as binding to a specific target, enzymatic activity, protein activation, and gene expression.

The present invention is also not limited to the use of fluorescent reporter molecules, but can also use luminescent, chemiluminescent, and other types of reporter molecules.

EXAMPLES

1. Reporter Sets and Relevant Image Analysis Methods

Non-limiting examples of reporter set types, and cellular events reported on by them:

a. Multiple transcription factor translocations to a common cell compartment, such as from the cytoplasm to the nucleus, using transcription factor-fluorescent protein chimeras, antibodies, or combinations thereof. Fluorescent signals from this reporter set are measured using any method for measuring translocation from the cytoplasm to the nucleus, such as those disclosed in U.S. Pat. No. 5,989,835, WO 98/38490, and WO 00/17643, and those described below.

b. Multiple receptor internalizations from the cell surface to the cell interior using receptor-fluorescent protein chimeras, fluorescent ligands for the receptors, antibody tags, or any combination thereof. Fluorescent signals from this reporter set would be measured using any method for measuring translocation from the cell surface to the inside of the cell, such as those disclosed in WO 00/03246 and described below.

c. Multiple viral infections using fluorescently tagged virions, viral-expressed fluorescent protein (such as GFP), antibodies to viral protiens, or any combination thereof, where infection is tracked by expression of GFP and its diffusion into the nucleus, or specific viral proteins translocate into the nucleus upon viral infection of the cell. Fluorescent signals from this reporter set would be measured using any method for measuring translocation from the cytoplasm to the nucleus, such as those disclosed in U.S. Pat. No. 5,989,835, WO 98/38490, and WO 00/17643, and those described below.

d. Evaluation of activation of cell stress pathways. A number of signal transduction factors are involved in cell stress pathways including kinases such as, JNK, p38 MAPK, MAPKAP2, Rsk B, and transcription factors ATF-2, ATF-1, and NFKB, as well as other components. Fluorescent signals from this reporter set are measured using any method for measuring translocation from the cytoplasm to the nucleus, such as those disclosed in U.S. Pat. No. 5,989,835, WO 98/38490, and WO 00/17643, and those described below. Thus, a screen of a library of compounds can assess which ones lead to activation of cell stress pathways. Pathway-specific composite assays would be typically made up of key sentinel targets of the specific pathway of interest.

e. Evaluation of activation of different cell stress pathways. There are multiple cell stress pathways, which could be differentially assessed. Two basic pathways include p38 MAPK and JNK. The p38 MAPK pathway can be assessed by using a first reporter set comprising fluorescent reporters of p38 MAPK, MAPKAP2, and HSP27. The JNK pathway can be assessed by using a second reporter set comprising fluorescent reporters of JNK, c-Jun, and ATF-2. In this example, assaying the p38 MAPK pathway in a first channel and the JNK pathway in a second channel could assess selectivity of one pathway over the other. Fluorescent signals from this reporter set are measured using any method for measuring translocation from the cytoplasm to the nucleus, such as those disclosed in U.S. Pat. No. 5,989,835, WO 98/38490, and WO 00/17643, and those described below.

f. Evaluation of activation of mitogenic pathways. A number of signal transduction factors are involved in mitogenic pathways leading to cell proliferation including kinases, such as ERK/MAPK, Rsk 1, Rsk 2, Rsk 3, Mnk 2, and transcription factors, such as CREB, c-Fos, and srf. Fluorescent signals from this reporter set are measured using any method for measuring translocation from the cytoplasm to the nucleus, such as those disclosed in U.S. Pat. No. 5,989,835, WO 98/38490, and WO 00/17643, and those described below. Thus, a screen on a library of compounds can assess which ones lead to activation of cell proliferation pathways.

g. Evaluation of activation of cell stress vs mitogenic pathways. A simultaneous profiling of a compound library in terms of those that activate stress pathways vs mitogenic pathways could be accomplished as a primary screen, using two or more reporter sets as described above. Fluorescent signals from these reporter sets are measured using any method for measuring translocation from the cytoplasm to the nucleus, such as those disclosed in U.S. Pat. No. 5,989,835, WO 98/38490, and WO 00/17643, and those described below. This primary screen would identify compounds to be deconvolved by stress targets and/or mitogenic targets, depending on the organization of the reporter sets.

h. Combined tracking of cell stress, apoptosis, and viral infection: Fluorescent signals from this reporter set would be measured using any method for measuring translocation from the cytoplasm to the nucleus, such as those disclosed in U.S. Pat. No. 5,989,835, WO 98/38490, and WO 00/17643, and those described below. Examples of appropriate fluorescent reporter molecules for this type of reporter set include, but are not limited to:
  1. Cell stress: NFKB antibody (Zymed, Inc.) or an engineered Nf-kB fluorescent protein chimera;
  2. Apoptosis: Caspase 3,6, or 8 biosensor (See, for example, WO WO 00/26408; Cohen (1997), *Biochemical J.* 326:1–16; Liang et al. (1997), *J. of Molec. Biol.* 274:291–302))
  3. Viral infection: For example, a fluorescent virion such as adenovirus-GFP, where infection is tracked by expression of GFP and its diffusion into the nucleus; alternatively, antibodies against specific viral proteins that translocate into the nucleus upon viral infection of the cell can be used.

i. Combined tracking of multiple organelle states: Fluorescent signals from this reporter set can be measured using any method for measuring changes in organelle mass, including but not limited to those disclosed in WO 00/50872 and WO/00/70342, incorporated by reference herein in their entirety, and those described below. Examples of appropriate fluorescent reporter molecules for this type of reporter set include, but are not limited to:
  1. MITOTRACKER® green (Molecular Probes Eugene, Oreg.) to measure mitochondrial mass,
  2. LYSOTRACKER™ green (Molecular Probes Eugene, Oreg.) to measure lysosomal mass, and
  3. Fluorescent protein targeted to peroxisomes to measure peroxisomal mass. (See, for example, WO/00/70342; Amery et al., Biochem J. 336:367–371 (1998); Wiemer et al., J. Cell Biol. 136:71–80 (1997) for construction of such targeted proteins).

j. Cytoskeletal integrity: Fluorescent signals from this reporter set can be measured using any method for measuring morphology (such as, but not limited to, polymerization, bundling, etc.) of a cytoplasmic structure, such as those disclosed in WO 98/38490 and WO 00/17643, and those described below. Examples of appropriate fluorescent reporter molecules for this type of reporter set include, but are not limited to:
  1. Fluorescently labeled tubulin to stain microtubules (WO 98/38490); and
  2. Fluorescently labeled phalloidin to stain F-actin (microfilaments) (Molecular Probes Eugene, Oreg.).

k. Macromolecule translocation from Golgi to cell surface: Fluorescent signals from this reporter set can be measured using any method for measuring translocation of a reporter from the cytoplasm to the cell surface, such as those described in WO 98/38490. A variation of this assay comprises assaying accumulation in the Golgi of proteins blocked from secretion (see below). Examples of appropriate fluorescent reporter molecules for this type of reporter set include, but are not limited to:
  1. Antibodies to cytokines, such as interleukins (Available, for example, from Biogenesis, Ltd. UK)
  2. Antibodies to extracellular proteases such as collagenases and elastase (Available, for example, from Biogenesis, Ltd. UK)
  3. Antibodies to growth factors such as vascular endothelial growth factor (VEGF), endothelial growth factor (EGF), and nerve growth factor (NGF) (Available, for example, from Biogenesis, Ltd. UK)

l. Cytoplasm to membrane translocation: Fluorescent signals from this reporter set can be measured using any method for measuring translocation of a reporter from the cytoplasm to the cell membrane, such as those described in WO 98/38490. Examples of appropriate fluorescent reporter molecules for this type of reporter set include, but are not limited to:
  1. GLUT4 antibody or fluorescent protein chimera (reporter of glucose transport) (FabGennix, Inc.),
  2. Beta-arrestin fluorescent protein chimera (reporter of GPCR activation) (Barak et al. (1997), *J. Biol. Chem.* 272:27497–27500; Daaka et al. (1998), *J. Biol. Chem.* 273:685–688), or antibodies to beta arrestin,
  3. ARF 6 (reporter of membrane ruffling) antibody or fluorescent protein chimera,
  4. Fluorescent protein biosensor of profilin membrane binding(Federov et al.(1994), *J. Molec. Biol.* 241: 480–482; Lanbrechts et al. (1995), *Eur. J. Biochem.* 230:281–286), and
  5. Rho protein (Self et al. (1995), *Methods in Enzymology* 256:3–10; Tanaka et al. (1995), *Methods in Enzymology* 256:41–49)

m. Loss of signal from the cell surface: Fluorescent signals from this reporter set can be measured using any method for measuring loss of signal from a cell surface, such as those described in WO 01/35072. Examples of appropriate fluorescent reporter molecules for this type of reporter set include, but are not limited to any combination of antibodies to: external epitopes of amyloid precursor protein (APP) (Available, for example, from Biogenesis, Ltd. UK), an external loop of any receptor, N-acetyl glucosamine (NAG) (Amersham; Molecular Probes) integrins (Available, for example, from Biogenesis, Ltd. UK), MHC complexes (Available, for example, from Abcam, Ltd. UK).

2. Details of Image Analysis Examples for Primary and Secondary Screening Assays The primary and secondary screens of the instant invention can comprise any high content cell based screen or combination of high content screens that a user wants to implement and can utilize the appropriate combination of fluorescent reporter molecules required, including but not limited to those described below, and those described in U.S. Pat. Nos. 5,989,835 and 6,103,479, as well as published PCT application nos. WO 98/38490, WO 00/03246, WO 00/17643, WO 00/26408, WO 00/50872, WO/00/70342, WO 00/17624, WO/00/60356, WO/00/70342, WO 01/11340, WO 01/11341, WO 01/35072, and WO 01/42786.

By way of non-limiting examples, the following screening and image analysis methods can be used for various primary and/or secondary screens according to the methods of the present invention:

1. Cytoplasm to nuclear translocation: (A preferred embodiment of the method is described in detail in U.S. Pat. No. 5,989,835) A nuclear image is acquired and preferably thresholded to create a nuclear mask. A cytoplasmic image is created using either the nuclear image or the fluorescent signals from the fluorescent reporter molecules in the reporter set. Preferably, a cytoplasmic mask is created. Translocation of the fluorescent reporter molecules in an appropriate reporter set(s) between the nucleus and cytoplasm can then be determined by detecting fluorescent signals in the nuclear mask and cytoplasmic mask in the presence and absence of the one or more test compounds.

2. Receptor internalization: (A preferred embodiment of the method is described in detail in WO 00/03246) A nuclear image is acquired and preferably, thresholded to create a nuclear mask. Fluorescent signals from the fluorescent reporter molecules in the reporter set are used to create a fluorescent reporter image, and preferably a mask is created from the fluorescent reporter image. Valid internalization of fluorescent reporter molecules in an appropriate reporter set(s), and the effect of the one or more test compounds on such receptor internalization, are determined using the fluorescent reporter mask. A preferred method for assaying receptor internalization and trafficking is carried out by detecting fluorescent reporter molecule trafficking through the endosomal system.

3. Changes in Mitochondrial Mass/Potential: (A preferred embodiment of the method is described in detail in WO 00/50872) Combining the ability to normalize to mitochondrial mass with a measure of the membrane potential allows independent assessment of both parameters. In a non-limiting example, mitochondrial membrane potential is measured by labeling mitochondria with a combination of fluorescent reporter molecules, such as MITOTRACKER® Green FM and MITOTRACKER® Red (Molecular Probes, Inc). In this example, MITOTRACKER® Red labeling is proportional to both mass and membrane potential. MITOTRACKER® Green FM labeling is proportional to mass. The ratio of MITOTRACKER® Red signal to the MITOTRACKER® Green FM signal provides a measure of mitochondrial membrane potential (Poot and Pierce, 1999). This ratio normalizes the mitochondrial mass with respect to the MITOTRACKER® Red signal.

4. Cytoskeletal integrity: (Preferred embodiments of the method are described in detail in WO 98/38490, WO 00/17643, and WO 00/50872.) In a non-limiting example, quantitation of f-actin content and assembly state is accomplished by measuring the intensity of phalloidin staining (or other fluorescent reporter specific for actin) around a nuclear mask, and quantitation of microtubule polymerization state is preferably accomplished by measuring the intensity of β-tubulin staining (or other fluorescent reporter specific for tubulin) around a nuclear mask.

5. Changes in organelle mass: (A preferred embodiment of the method is described in detail in WO/00/70342.) In a non-limiting example, a whole cell mask is created using an appropriate cell indicator marker such as phalloidin or chloromethylfluorescein diacetate (CMFDA), and adaptively thresholding the image obtained. The whole cell mask generated can then be applied to the image obtained for the fluorescent reporter molecules in an appropriate reporter set specific to the organelle of interest to obtain a measurement for abundance/mass of the organelle, based on the integrated fluorescence intensity.

6. Cytoplasm to cell membrane translocation: (A preferred embodiment of the method is described in detail in WO 98/38490.) In a non-limiting example, masks are created of the plasma membrane and the cytoplasm. These masks are used to mask the image of the fluorescent reporter molecules in an appropriate reporter set(s) that translocate from the cytoplasm to the cell surface. The integrated brightness per unit area under each mask is used to form a translocation quotient by dividing the plasma membrane integrated brightness/area by the cytoplasmic integrated brightness/area. By comparing the translocation quotient values from control and experimental wells, the percent translocation is calculated for each test compound or compounds.

7. Translocation between the endoplasmic reticulum and the Golgi: (A preferred embodiment of the method is described in detail in WO 98/38490.) In a non-limiting example, masks of the endoplasmic reticulum and the Golgi domains are created and used to mask the image of the fluorescent reporter molecules in an appropriate reporter set(s) whose activation is measured by translocation between the endoplasmic reticulum and the Golgi. The integrated brightness per unit area under each mask is used to form a translocation quotient by dividing the endoplasmic reticulum integrated brightness/area by the Golgi integrated brightness/area. By comparing the translocation quotient values from control and experimental wells, the percent translocation is calculated for each test compound or compounds.

Alternatively, reagents that block protein secretion and cause accumulation of the proteins in the Golgi (BioSource, Camarillo, Calif.) can be used to block transport of intracellular cytokines. Thus one can assay for compounds that stimulate cytokine production by using the reagent to cause accumulation of the cytokines in the Golgi, where they can be visualized using the above methods.

8. Cell Spreading: (A preferred embodiment of the method is described in detail in WO 01/42786.) In a non-limiting example, the fluorescent reporter molecules of an appropriate reporter set are used to create a cytoplasmic image of the cell, which is used to create a cytoplasmic mask. Various cell-based morphological features can then be automatically calculated, including cell area, cell perimeter, cell shape, cell aggregate intensity, and cell average intensity. These morphological features provide a measure of the effect of the test stimulus on cell spreading.

9. Neurite outgrowth (or other cellular outgrowth): (A preferred embodiment of the method is described in detail in WO 01/11340.) In a non-limiting example, a nuclear mask is created as described above, and the degree of neurite outgrowth (or other cellular outgrowth) is identified by classifying the fluorescent images from the fluorescent reporter molecules in an appropriate reporter set(s) into two groups: the cell body; and neurites (or outgrowths) All of the outgrowths and processes emerging from the cell body are classified as neurites (outgrowths). The results obtained from applying the present method allow the user to define and classify the neurites (outgrowths) according to their own classification guidelines. One can identify the characteristics and/or degree of outgrowth in the well and for individual cells and cell clusters.

10. Cell State Analysis: (A preferred embodiment of the method is described in detail in WO 01/35072.) In a non-limiting example, all the cells in the population are identified by, for example, a nuclear stain, and the fluorescent report molecules in an appropriate reporter set(s) are specific for a particular physiological state of the cells, and thus an appropriate reporter set reports on multiple different physiological states. The states can be mutually exclusive (e.g. the cell is alive or dead) or the cell can be in several different states at the same time. For example, in a brain cell population, different fluorescent reporter molecules in the reporter set could assess whether the cell (1) is a neuron, (2) is alive, and (3) expresses certain neuron-specific proteins. Cross correlation analysis between the different states provides a more complete characterization of the different states of the individual cells in a population. In a non-limiting example, a nuclear stain is used to identify all cells, and the fluorescent reporter molecules in an a first reporter set are specific for either live or dead cells The basis of the screen is that when cells die (or are dying) their membranes become leaky and permeable to large macromolecules. This allows the entry of membrane-impermeant markers, including nucleic-acid dyes such as propidium iodide, and the loss of soluble cytoplasmic markers, such as esterases. Cytoplasmic esterase activity in live cells causes the retention of and converts the non-fluorescent live-cell indicator chloromethyl fluorescein diacetate (CMFDA) (Molecular Probes, Inc.) into a fluorescent product. Dead cells can be identified by the presence of nuclear propidium iodide ("PI") (Molecular Probes, Inc.) fluorescence in the red channel, and live cells can be identified by cytoplasmic CMFDA fluorescence in the green channel.

3. Specific Examples

In this example, two reporter sets were used, each containing two fluorescent reporter molecules. The first reporter set consisted of ALEXA FLUOR™ 488 conjugated secondary antibodies (Molecular Probes, Inc.), which both emit fluorescence detectable in the green channel. These secondary antibodies were used to bind to primary antibodies against extracellular (signal) regulated kinase (ERK) (Cell Signaling Technologies, Inc.) and Nf-kB (Zymed, Inc.). The second reporter set consisted of ALEXA FLUOR™ 568 conjugated secondary antibodies (Molecular Probes, Inc.) which both emit fluorescence detectable in the red channel. These secondary antibodies were used to bind to primary antibodies against c-jun and p38.

In this experiment, the transcription factors under investigation translocate from the cytoplasm to the nucleus upon activation. Therefore, the fluorescent reporter molecules, which indirectly bind to the transcription factors, can be used to monitor the distribution of the transcription factors within the cell. However, each reporter reports on a different cellular event (i.e.: ERK translocation, Nf-kB translocation, c-jun translocation, and p38 translocation).

Swiss 3T3 cells in EMEM culture medium were plated in 96 well plates, at a plating density of 3,500 cells per well, and allowed to incubate overnight. Various columns of wells in the microplate were treated with TNF (known to activate NFKB), PMA (known to activate ERK and p38), anisomysin (known to activate p38 and c-jun), or were left untreated, and the cells were incubated at 37° C. in 5% $CO_2$ for 30 minutes. Cells were washed with 37° C. PBS (200 µl per well), which was then aspirated prior to adding 200 µl of 37° C. 3.7% formaldehyde in PBS. The cells were incubated at room temperature for 30 minutes, followed by washing twice with permeabilization buffer (0.1% Triton X-100 in PBS), leaving the second wash on for 15 minutes. The cells were then washed once with 200 µl of PBS at room temperature, the PBS was removed, and a solution of primary antibodies (as listed in Table 1) was added in a volume of 50 µl. The antibody incubation was carried out at room temperature for one hour, followed by 2 washes with 0.1% Tween 20 in PBS, followed by incubation with the secondary antibodies, as listed in Table 1. The secondary antibodies were added to obtain a final dilution of 1:100, plus Hoechst dye (1:2000) to label nuclei and thus identify the cells. This incubation proceeded for one hour, followed by two washes with each of Tween 20 and PBS. The plate was then sealed and stored at 4° C. until scanning on the ARRAYSCAN® HCS system (Cellomics, Inc. Pittsburgh, Pa.).

TABLE 1

| Target | Channel | Fluorescent reporter molecule | | Marker |
| --- | --- | --- | --- | --- |
| | | 1° antibody | 2° antibody | |
| nucleus | 1 - blue | — | — | Hoechst |
| ERK | 2 - green | Rabbit anti-ERK (p) | Goat anti-rabbit ALEXA FLUOR ® 488 | |
| NFkB | 2 - green | Rabbit anti-NFkB (p) | Goat anti-rabbit ALEXA FLUOR ® 488 | |
| cJUN | 3 - red | Mouse anti-cJUN (p) | Goat anti-mouse ALEXA FLUOR ® 568 | |
| P38HOG | 3 - red | Mouse anti-p38 (p) | Goat anti-mouse ALEXA FLUOR ® 568 | |

No deconvolution was necessary, as the known effects of compounds were being tested. The results in the figures thus represent the data generated from the primary screen.

Expected Results

The various possible outcomes of such a screen are given in Table 2, along with an interpretation of results and follow-up steps. Average hit rates in most good high content cell based screens do not exceed 0.1% to 1.0% of compounds screened, and therefore most of the wells will be negative with no requirement for secondary screening.

TABLE 2

| outcome | Potential scenarios | Follow up (Deconvolution) | % events |
| --- | --- | --- | --- |
| No translocation | All negative | none | 96–99 |
| Green trans | 1. ERK pos/NFkB neg/cJUN & p38 neg<br>2. NFkB pos/ERK neg/cJUN & p38 neg<br>3. NFkB &ERK pos/cJUN & p38 neg | Matrix test ERK/NFkB | 1–2 |
| Red trans | 1. cJUN pos/p38 neg/ERK & NFkB neg<br>2. p38 pos/cJUN neg/ERK & NFkB neg<br>3. p38 & cJUN pos/ERK & NFkB neg | Matrix test p38/cJUN | 1–2 |
| Green/Red trans | 1. ALL pos<br>2. ERK pos/NFkB neg/cJUN & p38 pos<br>3. ERK neg/NFkB pos/cJUN & p38 pos<br>4. ALL OTHER COMBINATIONs | Matrix test both ERK/NFkB p38/cJUN or consider them to be too nonspecific | 1–2 |

Results

Figure 5:
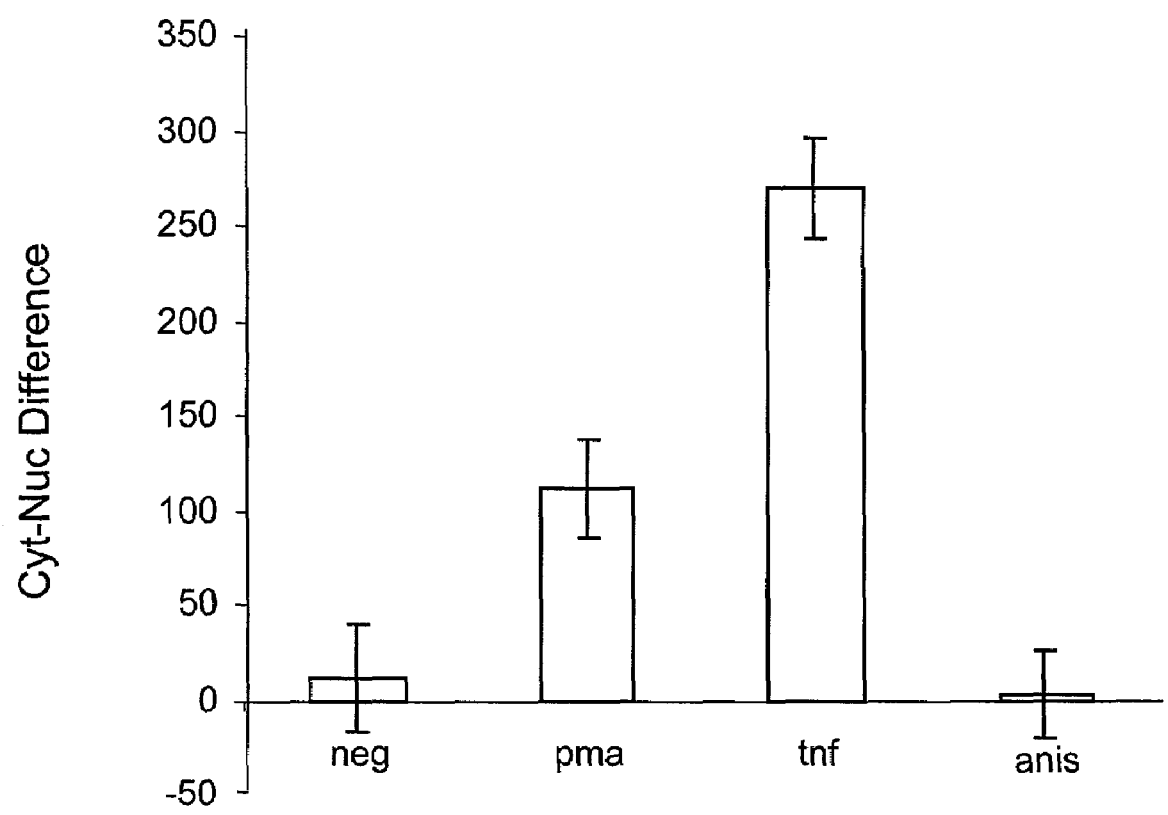
FIG. 5 is a bar graph demonstrating that both NFkB and ERK specific translocations can be observed in response to TNF and PMA in the green channel, while anisomysin has no effect on translocation in the green channel over negative controls.
Figure 6:
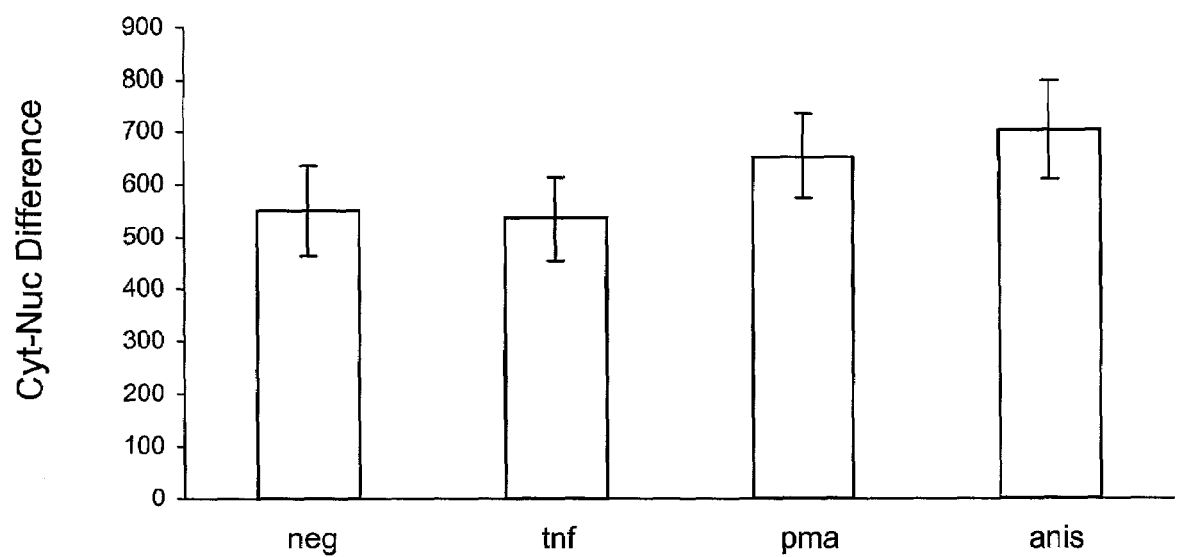
FIG. 6 is a bar graph demonstrating an increase in translocation for p38 and c-jun in response to PMA and anisomysin but not TNF in the red channel.

Below are two summary graphs of the translocation observed for the cells exposed to various stimulators FIG. 5 depicts measurements from the green channel and clearly shows that both NFkB and ERK specific translocations can be observed (increase in differences between cytoplasm and nuclear localization) in response to TNF and PMA, while anisomysin has no effect on translocation in the green channel over negative controls. FIG. 6 summarizes the data in the red channel, and shows an increase in translocation for p38 and c-jun in response to PMA and anisomysin but not TNF. Thus, these results clearly demonstrate the feasibility of the methods of the present invention.

We claim:

1. A high throughput method of high content cell based screening assays, comprising:
   a) providing at least a first array of locations that contain multiple cells, wherein the cells comprise a first reporter set, wherein the first reporter set comprises at least a first fluorescent reporter molecule and a second fluorescent reporter molecule, wherein the fluorescent reporter molecules in the first reporter set
      i) report on different cellular events;
      ii) exhibit phenotypically similar behavior; and
      iii) emit fluorescence at wavelengths detectable in at least a first channel of a fluorescence detection devices, wherein the fluorescence emitted from the fluorescent reporter molecules in the first reporter set are not optically distinguishable in the first channel;
   b) conducting a primary screen that comprises imaging the at least first array of locations in high content mode to obtain fluorescent signals in the first channel from the fluorescent reporter molecules in the first reporter set, wherein the imaging occurs either before, after, and/or simultaneously with contacting of the at least first array of locations with one or more test compounds;
   c) detecting test compound induced changes in the fluorescent signals in the first channel from the fluorescent reporter molecules in the first reporter set, wherein a test compound induced change in the fluorescent signals in the first channel indicates an effect of the one or more test compounds on one or more cellular events reported on by the fluorescent reporter molecules in the first reporter set; and
   d) deconvolving the test compound induced changes, wherein the deconvolving comprises conducting one or more secondary screens, wherein at least one of the secondary screens comprises a method selected from the group consisting of:
      i) screening positive locations on the first array of locations in which test compound induced changes were detected in the primary screen, wherein the cells in the positive locations and any control locations to be screened in the secondary screen are further contacted with two or more further fluorescent reporter molecules that are optically distinguishable from each other and from the fluorescent reporter molecules in the first reporter set, wherein at least one of the further fluorescent reporter molecules reports on the same cellular event as the first fluorescent reporter molecule, and wherein at least one of the further fluorescent reporter molecules reports on the same cellular event as the second fluorescent reporter molecule; and
      ii) screening an at least second array of locations and an at least third array of locations that contain multiple cells, wherein the cells on the at least second array of locations comprise the first fluorescent reporter molecule and not the second fluorescent reporter molecule; and wherein the cells on the at least third array of locations comprise the second fluorescent reporter molecule and not the first fluorescent reporter molecule; wherein the deconvolving comprises contacting the at least second array of locations and the at least third array of locations with only those test compounds that produced test compound induced changes during the primary screen, and optionally with one or more control compounds.

2. The method of claim 1, wherein deconvolving comprises:
   A) providing at least a second array of locations that contain multiple cells, wherein the cells on the at least second array of locations comprise the first fluorescent reporter molecule and not the second fluorescent reporter molecule;
   B) providing at least a third array of locations that contain multiple cells, wherein the cells on the at least third array of locations comprise the second fluorescent reporter molecule and not the first fluorescent reporter molecule;
   C) imaging the at least second array of locations and the at least third array of locations in high content mode to obtain fluorescent signals from the first fluorescent reporter molecule on the at least second array of locations and fluorescent signals from the second fluorescent reporter molecule on the at least third array of locations, wherein the imaging occurs either before, after, and/or simultaneously with contacting of the at least second array of locations and the at least third array of locations with one or more test compounds that produced test compound induced changes during the primary screen, and optionally with one or more control compounds; and
   D) detecting test compound induced changes in the fluorescent signals from the first fluorescent reporter molecule on at least second array of locations and/or the fluorescent signals from the second fluorescent reporter molecule on the at least third array of locations, wherein a test compound induced change in the fluorescent signals from the first fluorescent reporter molecule on the at least second array of locations indicates an effect of the one or more test compounds on the cellular event reported on by the first fluorescent reporter molecule, and wherein a test compound induced change in the fluorescent signals from the second fluorescent reporter molecule on the at least third array of locations indicates an effect of the one or more test compounds on the cellular event reported on by the second fluorescent reporter molecule.

3. The method of claim 1, wherein deconvolving comprises
   A) contacting the cells in only positive locations on the at least first array of locations in which a test compound induced change was detected, and optionally control locations, with at least a third fluorescent reporter molecule and a fourth fluorescent reporter molecule, wherein the third fluorescent reporter and the fourth fluorescent molecule are optically distinguishable from each other and from the first fluorescent reporter molecule and the second fluorescent reporter molecule, and wherein the third fluorescent reporter molecule reports on the same cellular event as the first fluorescent reporter molecule, and wherein the fourth fluorescent reporter molecule reports on the same cellular event as the second fluorescent reporter molecule;

B) imaging the positive locations on the at least first array of locations, in high content mode to obtain fluorescent signals from the third fluorescent reporter molecule and the fourth fluorescent reporter molecule; and C) detecting test compound induced changes in the fluorescent signals from the third fluorescent reporter molecule and/or the fluorescent signals from the fourth fluorescent reporter molecule, wherein a test compound induced change in the fluorescent signals from the third fluorescent reporter molecule indicates an effect of the one or more test compounds on the cellular event reported on by the first fluorescent reporter molecule, and wherein a test compound induced change in the fluorescent signals from the at least fourth fluorescent reporter molecule indicates an effect of the one or more test compounds on the cellular event reported on by the second fluorescent reporter molecule.

4. The method of claim 1, wherein the first reporter set further comprises at least a third fluorescent reporter molecule.

5. The method of claim 4, wherein the deconvolving comprises completely deconvolving the test compound induced changes in the fluorescent signals from the fluorescent reporter molecules in the first reporter set.

6. The method of claim 5, wherein completely deconvolving comprises:

A) providing at least a second array of locations that contain multiple cells, wherein the cells on the at least second array of locations comprise the first fluorescent reporter molecule and not the second fluorescent reporter molecule or the third fluorescent reporter molecule;

B) providing at least a third array of locations that contain multiple cells, wherein the cells on the at least third array of locations comprise the second fluorescent reporter molecule and not the first fluorescent reporter molecule or the third fluorescent reporter molecule;

C) providing at least a fourth array of locations that contain multiple cells, wherein the cells on the at least fourth array of locations comprise the third fluorescent reporter molecule and not the first fluorescent reporter molecule or the second fluorescent reporter molecule;

D) imaging the at least second array of locations, the at least third array of locations, and the at least fourth array of locations in high content mode to obtain fluorescent signals from the first fluorescent reporter molecule on the at least second array of locations, fluorescent signals from the second fluorescent reporter molecule on the at least third array of locations, and fluorescent signals from the third fluorescent reporter molecule on the at least fourth array of locations, wherein the imaging occurs either before, after, and/or simultaneously with contacting of the at least second array of locations, the at least third array of locations, and the at least fourth array of locations with one or more test compounds that produced test compound induced changes during the primary screen, and optionally with one or more controls; and E) detecting test compound induced changes in the fluorescent signals from the first fluorescent reporter molecule on the at least second array of locations, the second fluorescent reporter molecule on the at least third array of locations, and/or the third fluorescent reporter molecule on the at least fourth array of locations, wherein a test compound induced change in the fluorescent signals from the first fluorescent reporter molecule on the at least second array of locations indicates an effect of the one or more test compounds on the cellular event reported on by the first fluorescent reporter molecule, wherein a test compound induced change in the fluorescent signals from the second fluorescent reporter molecule on the at least third array of locations indicates an effect of the one or more test compounds on the cellular event reported on by the second fluorescent reporter molecule, and wherein a test compound induced change in the fluorescent signals from the third fluorescent reporter molecule on the at least fourth array of locations indicates an effect of the one or more test compounds on the cellular event reported on by the third fluorescent reporter molecule.

7. The method of claim 5, wherein completely deconvolving comprises

A) contacting the cells in only positive locations on the at least first array of locations in which a test compound induced change was detected, with at least a fourth fluorescent reporter molecule, a fifth fluorescent reporter molecule, and a sixth fluorescent reporter molecule, wherein the fourth fluorescent reporter molecule, the fifth fluorescent reporter molecule, and the sixth fluorescent reporter molecule are optically distinguishable from each other and from the fluorescent reporter molecules in the first reporter set, and wherein the fourth fluorescent reporter molecule reports on the same cellular event as the first fluorescent reporter molecule, wherein the fifth fluorescent reporter molecule reports on the same cellular event as the second fluorescent reporter molecule, and wherein the sixth fluorescent reporter molecule reports on the same cellular event as the third fluorescent reporter molecule;

B) imaging the positive locations on the at least first array of locations, in high content mode to obtain fluorescent signals from the fourth fluorescent reporter molecule, the fifth fluorescent reporter molecule, and the sixth fluorescent reporter molecule; and C) detecting test compound induced changes in the fluorescent signals from the fourth fluorescent reporter molecule, the fluorescent signals from the fifth fluorescent reporter molecule, and/or the fluorescent signals from the sixth fluorescent reporter molecule, wherein a active test compound induced change in the fluorescent signals from the fourth fluorescent reporter molecule indicates an effect of the one or more test compounds on the cellular event reported on by the first fluorescent reporter molecule, wherein a test compound induced change in the fluorescent signals from the fifth fluorescent reporter molecule indicates an effect of the one or more test compounds on the cellular event reported on by the second fluorescent reporter molecule, and wherein a test compound induced change in the fluorescent signals from the sixth fluorescent reporter molecule indicates an effect of the one or more test compounds on the cellular event reported on by the third fluorescent reporter molecule.

8. The method of claim 4, wherein the deconvolving comprises partially deconvolving the test compound induced changes in the fluorescent signals from the fluorescent reporter molecules in the first reporter set.

9. The method of claim 8, wherein the partial deconvolving comprises deconvolving the test compound induced changes in the fluorescent signals from less than all of the fluorescent reporter molecules in the first reporter set.

10. The method of claim 9 wherein the partial deconvolving is done on the at least first array of locations.

11. The method of claim 9 wherein the partial deconvolving is done on an at least second array of locations.

12. The method of claim 1, wherein the cells further comprise at least a second reporter set, wherein the at least second reporter set comprises at least a third fluorescent reporter molecule and a fourth fluorescent reporter molecule, wherein the fluorescent reporter molecules in the second reporter set
  i) report on different cellular events;
  ii) exhibit phenotypically similar behavior; and
  iii) emit fluorescence at wavelengths detectable in at least a second channel of a fluorescence detection device, wherein the fluorescence emitted from the fluorescent reporter molecules in the second reporter set are not optically distinguishable in the second channel;
  wherein the primary screen further comprises imaging the at least first array of locations in high content mode to obtain fluorescent signals in the second channel from the fluorescent reporter molecules in the second reporter set; and
  wherein the detecting further comprises detecting test compound induced changes in the fluorescent signals in the second channel from the fluorescent reporter molecules in the second reporter set, wherein test compound induced changes in the fluorescent signals in the second channel from the fluorescent reporter molecules in the second reporter set indicate an effect of the one or more test compounds on one or more cellular events reported on by the at least second reporter set.

13. The method of claim 12, wherein the deconvolving comprises completely deconvolving the test compound induced chances in the fluorescent signals in the first channel from the fluorescent reporter molecules the first reporter set and the test compound induced changes in the fluorescent signals in the second channel from the fluorescent reporter molecules in the second reporter set.

14. The method of claim 13, wherein completely deconvolving comprises:
  A) providing at least a second array of locations that contain multiple cells, wherein the cells on the at least second array of locations comprise the first fluorescent reporter molecule and not the second fluorescent reporter molecule, the third fluorescent reporter molecule, or the fourth fluorescent reporter molecule;
  B) providing at least a third array of locations that contain multiple cells, wherein the cells on the at least third array of locations comprise the second fluorescent reporter molecule and not the first fluorescent reporter molecule, the third fluorescent reporter molecule, or the fourth fluorescent reporter molecule;
  C) providing at least a fourth array of locations that contain multiple cells, wherein the cells on the at least fourth array of locations comprise the third fluorescent reporter molecule and not the first fluorescent reporter molecule, the second fluorescent reporter molecule, or the fourth fluorescent reporter molecule;
  D) providing at least a fifth array of locations that contain multiple cells, wherein the cells on the at least fifth array of locations comprise the fourth fluorescent reporter molecule and not the first fluorescent reporter molecule, the second fluorescent reporter molecule, or the third fluorescent reporter molecule;
  E) imaging the at least second array of locations, the at least third array of locations, the at least fourth array of locations, and the at least fifth array of locations in high content mode to obtain fluorescent signals from the first fluorescent reporter molecule on the at least second array of locations, fluorescent signals from the second fluorescent reporter molecule on the at least third array of locations, fluorescent signals from the third fluorescent reporter molecule on the at least fourth array of locations, and fluorescent signals from the fourth fluorescent reporter molecule on the at least fifth array of locations, wherein the imaging occurs either before, after, and/or simultaneously with contacting of the at least second array of locations, the at least third array of locations, the at least fourth array of locations, and the at least fifth array of locations with one or more test compounds that produced test compound induced changes during the primary screen, and optionally with one or more control compounds; and
  F) detecting test compound induced changes in the fluorescent signals from the first fluorescent reporter molecule on the at least second array of locations, the second fluorescent reporter molecule on the at least third array of locations, the third fluorescent reporter molecule on the at least fourth array of locations, and/or the fourth fluorescent reporter molecule on the at least fifth array of locations, wherein a test compound induced change in the fluorescent signals from the first fluorescent reporter molecule on the at least second array of locations indicates an effect of the one or more test compounds on the cellular event reported on by the first fluorescent reporter molecule, wherein a test compound induced change in the fluorescent signals from the second fluorescent reporter molecule on the at least third array of locations indicates an effect of the one or more test compounds on the cellular event reported on by the second fluorescent reporter molecule, wherein a test compound induced change in the fluorescent signals from the third fluorescent reporter molecule on the at least fourth array of locations indicates an effect of the one or more test compounds on the cellular event reported on by the third fluorescent reporter molecule, and wherein a test compound induced change in the fluorescent signals from the fourth fluorescent reporter molecule on the at least fifth array of locations indicates an effect of the one or more test compounds on the cellular event reported on by the fourth fluorescent reporter molecule.

15. The method of claim 13, wherein completely deconvolving comprises
  A) contacting the cells in only positive locations on the at least first array of locations in which a test compound induced change was detected, and optionally control locations; with at least a fifth fluorescent reporter molecule, a sixth fluorescent reporter molecule, a seventh fluorescent reporter molecule, and an eighth fluorescent reporter molecule, wherein the fifth fluorescent reporter molecule, the sixth fluorescent molecule, the seventh fluorescent molecule, and the eighth fluorescent molecule are optically distinguishable from each other and from the fluorescent reporter molecules in the first reporter set and the second reporter set, and wherein the fifth fluorescent reporter molecule reports on the same cellular event as the first fluorescent reporter molecule, the sixth fluorescent molecule reports on the same cellular event as the second fluorescent molecule, the seventh fluorescent molecule reports on the same cellular event as the third fluorescent molecule, and wherein the eighth fluorescent reporter molecule reports on the same cellular event as the fourth fluorescent reporter molecule;

B) imaging the positive locations on the at least first array of locations, in high content mode to obtain fluorescent signals from the fifth fluorescent reporter molecule, the sixth fluorescent reporter molecule, the seventh fluorescent reporter molecule, and the eighth fluorescent reporter molecule; and C) detecting test compound induced changes in the fluorescent signals from the fifth fluorescent reporter molecule, the sixth fluorescent reporter molecule, the seventh fluorescent reporter molecule, and/or the eighth fluorescent reporter molecule, wherein a test compound induced change in the fluorescent signals from the fifth fluorescent reporter molecule indicates an effect of the one or more test compounds on the cellular event reported on by the first fluorescent reporter molecule, wherein a test compound induced change in the fluorescent signals from the sixth fluorescent reporter molecule indicates an effect of the one or more test compounds on the cellular event reported on by the second fluorescent reporter molecule, wherein a test compound induced change in the fluorescent signals from the seventh fluorescent reporter molecule indicates an effect of the one or more test compounds on the cellular event reported on by the third fluorescent reporter molecule, and wherein a test compound induced change in the fluorescent signals from the eighth fluorescent reporter molecule indicates an effect of the one or more test compounds on the cellular event reported on by the fourth fluorescent reporter molecule.

16. The method of claim 12, wherein the deconvolving comprises partially deconvolving the test compound induced changes in the fluorescent signals in the first channel from the fluorescent reporter molecules in the first reporter set and the test compound induced changes in the fluorescent signals in the second channel from the fluorescent reporter molecules in the at least second reporter set.

17. The method of claim 16, wherein the partial deconvolving comprises deconvolving the test compound induced changes in only one of (a) the fluorescent signals in the first channel from the fluorescent reporter molecules in the first reporter set; and (b) the fluorescent signals in the second channel from the fluorescent reporter molecules in the at least second reporter set.

18. The method of claim 16, wherein the partial deconvolving comprises deconvolving the test compound induced changes in the fluorescent signals in the first channel from less than all of the fluorescent reporter molecules in the first reporter set, and/or the test compound induced changes in the fluorescent signals in the second channel from less than all of the fluorescent reporter molecules in the at least second reporter set.

19. The method of claim 17 wherein the partial deconvolving is done on the at least first array of locations.

20. The method of claim 17 wherein the partial deconvolving is done on an at least second array of locations.

21. The method of claim 18 wherein the partial deconvolving is done on the at least first array of locations.

22. The method of claim 18 wherein the partial deconvolving is done on an at least second array of locations.

* * * * *